(12) United States Patent
Yao et al.

(10) Patent No.: US 8,664,182 B2
(45) Date of Patent: Mar. 4, 2014

(54) METHODS OF INHIBITING CANCER CELL GROWTH WITH HDAC INHIBITORS AND METHODS OF SCREENING FOR HDAC10 INHIBITORS

(75) Inventors: Tso-pang Yao, Chapel Hill, NC (US); Hitoshi Sasajima, Hokkaido (JP); Yoshiharu Kawaguchi, Aichi (JP); Kai Cui, Durham, NC (US); Chun-Hsiang Lai, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 13/129,035

(22) PCT Filed: Nov. 10, 2009

(86) PCT No.: PCT/US2009/063905
§ 371 (c)(1), (2), (4) Date: Dec. 8, 2011

(87) PCT Pub. No.: WO2010/056677
PCT Pub. Date: May 20, 2010

(65) Prior Publication Data
US 2012/0071417 A1    Mar. 22, 2012

Related U.S. Application Data

(60) Provisional application No. 61/113,859, filed on Nov. 12, 2008.

(51) Int. Cl.
| | | |
|---|---|---|
| *A61K 38/00* | (2006.01) | |
| *A61P 35/00* | (2006.01) | |
| *A01N 37/28* | (2006.01) | |
| *A61K 31/19* | (2006.01) | |
| *C07C 259/04* | (2006.01) | |

(52) U.S. Cl.
USPC ................. 514/19.3; 514/575; 562/623

(58) Field of Classification Search
USPC ................. 514/19.3, 575; 562/623
See application file for complete search history.

(56) References Cited

U.S. PATENT DOCUMENTS

| | | | |
|---|---|---|---|
| 6,416,777 | B1 | 7/2002 | Yaacobi |
| 6,713,081 | B2 | 3/2004 | Robinson et al. |
| 2004/0180075 | A1 | 9/2004 | Robinson et al. |
| 2007/0066527 | A1 | 3/2007 | Tezapsidis |
| 2007/0149466 | A1 | 6/2007 | Milburn et al. |
| 2008/0255149 | A1 | 10/2008 | Dobler et al. |
| 2008/0269259 | A1 | 10/2008 | Thompson et al. |

FOREIGN PATENT DOCUMENTS

| | | |
|---|---|---|
| WO | WO 2006/004360 | 1/2006 |
| WO | WO 2008/109498 | 9/2008 |
| WO | WO 2010/056677 | 5/2010 |

OTHER PUBLICATIONS

Hagelkruys et al. Handbook of Experimental Pharmacology, 2011, vol. 206, pp. 13-37.*
Carews et al. Blood, published online Mar. 2007, vol. 110, pp. 313-322.*
Butler et al. Cancer Research, 2000, vol. 60, pp. 5165-5170.*
Kim et al. The Journal of Biological Chemistry, Feb. 2008, vol. 283, No. 7, pp. 3731-3742.*
Dokmanovic et al. (2007) Mol. Cancer Res. 5: 981-9.
Drummond et al. (2005) Annu Rev Pharmacol Toxicol 45: 495-528.
Gallinari et al. (2007) Cell Res 17: 195-211.
Bali et al. (2005) J Biol Chem 280: 26729-26734.
Boyault et al. (2007) Genes Dev 21: 2172-2181.
Hubbert et al. (2002) Nature 417: 455-458.
Kawaguchi et al. (2003) Cell 115: 727-738.
Kovacs et al. (2005) Mol Cell 18: 601-607.
Kwon et al. (2007) Genes Dev 21: 3381-3394.
Kim et al. (2006) Mol Cell 23: 607-618.
Schwer et al. (2002) J. Cell Biol158: 647-657.
Duerr et al. (1993) Compar Bioehem Physiol106: 889-893.
Colombini (2007) Meth Cell Biol80: 241-260.
Towler et al. (2007) Cire Res 100: 328-341.
Liang et al. (2007) Nat Cell Biol 9, 218-224.
Hawley et al. (1996) J Biol Chern 271, 27879-27887.
Rostovtseva et al., (2005) J Bioenerg Biomem 37: 129-142.
Vander Heiden et al. (2000) Froc Natl Acad Sci USA 97: 4666-4671.
Yagoda et al. (2007) Nature 447: 864-868.
Blachly-Dyson et al., 1990.
Yehezkel et al., 2007.
Hess-Stumpp et al. (2007) Int J Biochem Cell Biol 39:1388-1405.
Hoyer-Hansen et al. (2007) Mol Cell 25: 193-205.
International Search Report and Written Opinion for Application No. PCT/US2009/063905 dated Feb. 24, 2010 (10 pages).

* cited by examiner

*Primary Examiner* — Samira Jean-Louis
(74) *Attorney, Agent, or Firm* — Michael Best & Friedrich LLP

(57) ABSTRACT

Methods of inhibiting cancer cell growth using HDAC10 inhibitors are provided. Methods of treating cancer in a subject using HDAC10 inhibitors are also provided. In certain embodiments, at least one second inhibitor selected from an autophagy inhibitor, an AMPK inhibitor, and methyl pyruvate is also used in the methods. Dose packs comprising HDAC10 inhibitors and at least one second inhibitor are provided. Methods of identifying HDAC10 inhibitors are also provided.

20 Claims, 14 Drawing Sheets

SEQUENCE LISTING

<160> NUMBER OF SEQ ID NOS: 6

<210> SEQ ID NO 1
<211> LENGTH: 25
<212> TYPE: RNA
<213> ORGANISM: Artificial Sequence
<220> FEATURE:
<223> OTHER INFORMATION: siRNA

<400> SEQUENCE: 1
uccagugugu aaggcagcug caucu                                           25

<210> SEQ ID NO 2
<211> LENGTH: 25
<212> TYPE: RNA
<213> ORGANISM: Artificial Sequence
<220> FEATURE:

<223> OTHER INFORMATION: siRNA

<400> SEQUENCE: 2
ugcgccguua guaaacaucg cucaa   25

<210> SEQ ID NO 3
<211> LENGTH: 19
<212> TYPE: RNA
<213> ORGANISM: Artificial Sequence
<220> FEATURE:
<223> OTHER INFORMATION: siRNA

<400> SEQUENCE: 3
cggguucugu guguucaac   19

<210> SEQ ID NO 4
<211> LENGTH: 25
<212> TYPE: RNA
<213> ORGANISM: Artificial Sequence
<220> FEATURE:
<223> OTHER INFORMATION: siRNA

<400> SEQUENCE: 4
ccgaccacau gaagcagcac gacuu   25

<210> SEQ ID NO 5
<211> LENGTH: 669
<212> TYPE: PRT
<213> ORGANISM: Homo sapiens

<400> SEQUENCE: 5

Met Gly Thr Ala Leu Val Tyr His Glu Asp Met Thr Ala Thr Arg Leu
1               5                   10                  15

Leu Trp Asp Asp Pro Glu Cys Glu Ile Glu Arg Pro Glu Arg Leu Thr
            20                  25                  30

Ala Ala Leu Asp Arg Leu Arg Gln Arg Gly Leu Glu Gln Arg Cys Leu
        35                  40                  45

Arg Leu Ser Ala Arg Glu Ala Ser Glu Glu Leu Gly Leu Val His
    50                  55                  60

Ser Pro Glu Tyr Val Ser Leu Val Arg Glu Thr Gln Val Leu Gly Lys
65                  70                  75                  80

Glu Glu Leu Gln Ala Leu Ser Gly Gln Phe Asp Ala Ile Tyr Phe His
                85                  90                  95

Pro Ser Thr Phe His Cys Ala Arg Leu Ala Ala Gly Ala Gly Leu Gln
            100                 105                 110

Leu Val Asp Ala Val Leu Thr Gly Ala Val Gln Asn Gly Leu Ala Leu
        115                 120                 125

Val Arg Pro Pro Gly His His Gly Gln Arg Ala Ala Ala Asn Gly Phe
    130                 135                 140

Cys Val Phe Asn Asn Val Ala Ile Ala Ala Ala His Ala Lys Gln Lys
145                 150                 155                 160

His Gly Leu His Arg Ile Leu Val Val Asp Trp Asp Val His Gly
                165                 170                 175

Gln Gly Ile Gln Tyr Leu Phe Glu Asp Asp Pro Ser Val Leu Tyr Phe
            180                 185                 190

Ser Trp His Arg Tyr Glu His Gly Arg Phe Trp Pro Phe Leu Arg Glu
        195                 200                 205

Ser Asp Ala Asp Ala Val Gly Arg Gly Gln Gly Leu Gly Phe Thr Val
    210                 215                 220

```
Asn Leu Pro Trp Asn Gln Val Gly Met Gly Asn Ala Asp Tyr Val Ala
225                 230                 235                 240

Ala Phe Leu His Leu Leu Leu Pro Leu Ala Phe Glu Phe Asp Pro Glu
            245                 250                 255

Leu Val Leu Val Ser Ala Gly Phe Asp Ser Ala Ile Gly Asp Pro Glu
            260                 265                 270

Gly Gln Met Gln Ala Thr Pro Glu Cys Phe Ala His Leu Thr Gln Leu
            275                 280                 285

Leu Gln Val Leu Ala Gly Gly Arg Val Cys Ala Val Leu Glu Gly Gly
            290                 295                 300

Tyr His Leu Glu Ser Leu Ala Glu Ser Val Cys Met Thr Val Gln Thr
305                 310                 315                 320

Leu Leu Gly Asp Pro Ala Pro Pro Leu Ser Gly Pro Met Ala Pro Cys
            325                 330                 335

Gln Ser Ala Leu Glu Ser Ile Gln Ser Ala Arg Ala Ala Gln Ala Pro
            340                 345                 350

His Trp Lys Ser Leu Gln Gln Gln Asp Val Thr Ala Val Pro Met Ser
            355                 360                 365

Pro Ser Ser His Ser Pro Glu Gly Arg Pro Pro Leu Leu Pro Gly
370                 375                 380

Gly Pro Val Cys Lys Ala Ala Ser Ala Pro Ser Ser Leu Leu Asp
385                 390                 395                 400

Gln Pro Cys Leu Cys Pro Ala Pro Ser Val Arg Thr Ala Val Ala Leu
            405                 410                 415

Thr Thr Pro Asp Ile Thr Leu Val Leu Pro Pro Asp Val Ile Gln Gln
            420                 425                 430

Glu Ala Ser Ala Leu Arg Glu Glu Thr Glu Ala Trp Ala Arg Pro His
            435                 440                 445

Glu Ser Leu Ala Arg Glu Ala Leu Thr Ala Leu Gly Lys Leu Leu
            450                 455                 460

Tyr Leu Leu Asp Gly Met Leu Asp Gly Gln Val Asn Ser Gly Ile Ala
465                 470                 475                 480

Ala Thr Pro Ala Ser Ala Ala Ala Thr Leu Asp Val Ala Val Arg
            485                 490                 495

Arg Gly Leu Ser His Gly Ala Gln Arg Leu Leu Cys Val Ala Leu Gly
            500                 505                 510

Gln Leu Asp Arg Pro Pro Asp Leu Ala His Asp Gly Arg Ser Leu Trp
            515                 520                 525

Leu Asn Ile Arg Gly Lys Glu Ala Ala Ala Leu Ser Met Phe His Val
530                 535                 540

Ser Thr Pro Leu Pro Val Met Thr Gly Gly Phe Leu Ser Cys Ile Leu
545                 550                 555                 560

Gly Leu Val Leu Pro Leu Ala Tyr Gly Phe Gln Pro Asp Leu Val Leu
            565                 570                 575

Val Ala Leu Gly Pro Gly His Gly Leu Gln Gly Pro His Ala Ala Leu
            580                 585                 590

Leu Ala Ala Met Leu Arg Gly Leu Ala Gly Gly Arg Val Leu Ala Leu
            595                 600                 605

Leu Glu Glu Asn Ser Thr Pro Gln Leu Ala Gly Ile Leu Ala Arg Val
            610                 615                 620

Leu Asn Gly Glu Ala Pro Pro Ser Leu Gly Pro Ser Ser Val Ala Ser
625                 630                 635                 640

Pro Glu Asp Val Gln Ala Leu Met Tyr Leu Arg Gly Gln Leu Glu Pro
            645                 650                 655
```

Gln Trp Lys Met Leu Gln Cys His Pro His Leu Val Ala
            660               665

<210> SEQ ID NO 6
<211> LENGTH: 2010
<212> TYPE: DNA
<213> ORGANISM: Homo sapiens

<400> SEQUENCE: 6

| | | | | | |
|---|---|---|---|---|---|
| atggggaccg | cgcttgtgta | ccatgaggac | atgacggcca | cccggctgct | ctgggacgac | 60 |
| cccgagtgcg | agatcgagcg | tcctgagcgc | ctgaccgcag | ccctggatcg | cctgcggcag | 120 |
| cgcggcctgg | aacagaggtg | tctgcggttg | tcagcccgcg | aggcctcgga | agaggagctg | 180 |
| ggcctggtgc | acagcccaga | gtatgtatcc | ctggtcaggg | agacccaggt | cctaggcaag | 240 |
| gaggagctgc | aggcgctgtc | cggacagttc | gacgccatct | acttccaccc | gagtaccttt | 300 |
| cactgcgcgc | ggctggccgc | aggggctgga | ctgcagctgg | tggacgctgt | gctcactgga | 360 |
| gctgtgcaaa | atgggcttgc | cctggtgagg | cctcccgggc | accatggcca | gagggcggct | 420 |
| gccaacgggt | tctgtgtgtt | caacaacgtg | gccatagcag | ctgcacatgc | caagcagaaa | 480 |
| cacgggctac | acaggatcct | cgtcgtggac | tgggatgtgc | accatggcca | ggggatccag | 540 |
| tatctctttg | aggatgaccc | cagcgtcctt | tacttctcct | ggcaccgcta | tgagcatggg | 600 |
| cgcttctggc | ctttcctgcg | agagtcagat | gcagacgcag | tggggcgggg | acagggcctc | 660 |
| ggcttcactg | tcaacctgcc | ctggaaccag | gttgggatgg | aaacgctga | ctacgtggct | 720 |
| gccttcctgc | acctgctgct | cccactggcc | tttgagtttg | accctgagct | ggtgctggtc | 780 |
| tcggcaggat | ttgactcagc | catcggggac | cctgaggggc | aaatgcaggc | cacgccagag | 840 |
| tgcttcgccc | acctcacaca | gctgctgcag | gtgctggccg | gcggccgggt | ctgtgccgtg | 900 |
| ctggagggcg | gctaccacct | ggagtcactg | gcggagtcag | tgtgcatgac | agtacagacg | 960 |
| ctgctgggtg | accggccccc | accctgtca | gggccaatgg | cgccatgtca | gagtgcccta | 1020 |
| gagtccatcc | agagtgcccg | tgctgcccag | gccccgcact | ggaagagcct | ccagcagcaa | 1080 |
| gatgtgaccg | ctgtgccgat | gagccccagc | agccactccc | cagaggggag | gcctccacct | 1140 |
| ctgctgcctg | ggggtccagt | gtgtaaggca | gctgcatctg | caccgagctc | cctcctggac | 1200 |
| cagccgtgcc | tctgccccgc | accctctgtc | cgcaccgctg | ttgccctgac | aacgccggat | 1260 |
| atcacattgg | ttctgccccc | tgacgtcatc | caacaggaag | cgtcagccct | gagggaggag | 1320 |
| acagaagcct | gggccaggcc | acacgagtcc | ctggcccggg | aggaggccct | cactgcactt | 1380 |
| gggaagctcc | tgtacctctt | agatgggatg | ctggatgggc | aggtgaacag | tggtatagca | 1440 |
| gccactccag | cctctgctgc | agcagccacc | ctggatgtgg | ctgttcggag | aggcctgtcc | 1500 |
| cacggagccc | agaggctgct | gtgcgtggcc | ctgggacagc | tggaccggcc | tccagacctc | 1560 |
| gcccatgacg | ggaggagtct | gtggctgaac | atcaggggca | aggaggcggc | tgccctatcc | 1620 |
| atgttccatg | tctccacgcc | actgccagtg | atgaccggtg | gtttcctgag | ctgcatcttg | 1680 |
| ggcttggtgc | tgcccctggc | ctatggcttc | cagcctgacc | tggtgctggt | ggcgctgggg | 1740 |
| cctggccatg | gcctgcaggg | ccccacgct | gcactcctgg | ctgcaatgct | tcggggggctg | 1800 |
| gcagggggcc | gagtcctggc | cctcctggag | gagaactcca | cccccagct | agcagggatc | 1860 |
| ctggcccggg | tgctgaatgg | agaggcacct | cctagcctag | gcccttcctc | tgtggcctcc | 1920 |
| ccagaggacg | tccaggccct | gatgtacctg | agagggcagc | tggagcctca | gtggaagatg | 1980 |
| ttgcagtgcc | atcctcacct | ggtggcttga | | | | 2010 |

METHODS OF INHIBITING CANCER CELL GROWTH WITH HDAC INHIBITORS AND METHODS OF SCREENING FOR HDAC10 INHIBITORS

CROSS-REFERENCE TO RELATED APPLICATIONS

This patent application is a national stage filing under 35 U.S.C. §371 of International Application No. PCT/US2009/063905 filed on Nov. 10, 2009, which claims priority to U.S. Provisional Application No. 61/113,859, filed on Nov. 12, 2008. These applications are incorporated herein by reference in their entireties.

STATEMENT OF GOVERNMENT SUPPORT

This invention was made with United States government support from the Department of Defense grant number W81XWH-09-1-0194. The United States government has certain rights in this invention.

BACKGROUND

Histone deacetylases (HDACs) have been extensively studied for their roles in transcriptional regulation and chromatin remodeling. HDACs are divided into four classes, according to sequence homology and domain organization (Dokmanovic et al. (2007) Mol. Cancer Res. 5: 981-9). Class I includes, for example, HDACs 1, 2, 3, and 8; class II includes, for example, HDACs 4, 5, 6, 7a, and 10; class III includes, for example, sirtuins; and class IV includes, for example, HDAC11.

HDACs have also drawn research interest because inhibitors of these enzymes display anti-tumor activities (reviewed in Drummond et al. (2005) Annu Rev Pharmacol Toxicol 45: 495-528). Certain HDAC inhibitors (HDACI) are at various stages of clinical trials for cancer patients, and at least one (SAHA/vorinostat) has been approved for clinical use (Gallinari et al. (2007) Cell Res 17: 195-211). Despite the potent activity of these compounds, the question of how HDAC inhibitors achieve their anti-tumor effect remains poorly understood. The well-established role for HDACs in histone acetylation and gene transcription has led to a general assumption that HDAC inhibitors achieve their therapeutic effects by affecting transcriptional programs important for proliferation and apoptosis.

The recent characterization of cytoplasmically-localized HDAC6 reveals that this class of enzymes has functions independent of histones and chromatin. (Bali et al. (2005) Biol Chem 280: 26729-26734; Boyault et al. (2007) Genes Dev 21: 2172-2181; Hubbert et al. (2002) Nature 417: 455-458; Kawaguchi et al. (2003) Cell 115: 727-738; Kovacs et al. (2005) Mol Cell 18: 601-607; Kwon et al. (2007) Genes Dev 21: 3381-3394). Supporting this view, a mass spectrometry-based proteomic analysis has identified a large number of acetylated proteins that have no apparent links to chromatin or gene transcription. (Kim et al. (2006) Mol Cell 23: 607-618) Among these non-nuclear acetylated proteins, some are mitochondrially localized, raising the possibility that certain mitochondrial functions may be regulated by reversible acetylation.

In addition to implying additional regulatory functions for HDACs outside the nucleus, these findings also raise the question as to whether non-genomic processes may also be affected by HDACI therapeutics.

SUMMARY

Methods of inhibiting cancer cell growth are provided. In certain embodiments, methods of inhibiting cancer cell growth comprise contacting a cell with at least one HDAC10 inhibitor and at least one second inhibitor selected from an autophagy inhibitor, an AMPK inhibitor, and methyl pyruvate. In certain embodiments, methods of inhibiting cancer cell growth comprise contacting a cell with an HDAC10 specific inhibitor. In certain embodiments, an HDAC10 inhibitor is an inhibitory RNA such as, for example, an siRNA.

In certain embodiments, methods of identifying HDAC10 inhibitors are provided. In certain such embodiments, cells are contacted with a test agent and the acetylation level of a voltage dependent anion channel (VDAC) in the contacted cells is compared to the acetylation level of a VDAC in control cells. In certain embodiments, an increase in the acetylation level of a VDAC in the contacted cells relative to the acetylation level of a VDAC in the control cells is indicative of the test agent being an HDAC10 inhibitor.

In certain embodiments, methods of treating an individual with cancer are provided. In certain such embodiments, the methods include administering at least one HDAC10 specific inhibitor to the individual with cancer. In certain embodiments, the method further comprises administering at least one second inhibitor selected from an autophagy inhibitor, an AMPK inhibitor, and methyl pyruvate.

In certain embodiments, a dose pack comprising a first dosage comprising an HDAC10 inhibitor and a second dosage comprising a second inhibitor selected from an autophagy inhibitor, an AMPK inhibitor, and methyl pyruvate is provided.

DESCRIPTION OF THE FIGURES

FIG. 1A-B are photographs of A549 cells infected with retrovirus expressing control (A) or HDAC10 specific siRNA (B). FIG. 1C is a graph showing the percent cell death in Hela cells cotransfected with either a control siRNA (cKD) or HDAC10-siRNA (HD10-KD), and either a vector expressing GFP or a vector expressing mouse HDAC10, as indicated. FIG. 1D is a photograph of a Western blot for p27, p21, HDAC, and actin after treatment Hela with trichostatin A (TSA) or an HDAC10 siRNA.

FIG. 2A is a set of photographs showing immunostaining of mitochondrial HSP70 (a) and HDAC10-int190 (b). Cell nuclei are shown in (c). FIG. 2B is a set of photographs showing detection of mitochondria with MitoTracker Red CMXRos (a) and immunostaining with an anti-HDAC10 antibody (int190) (b) following transfection with an siRNA to HDAC10. Arrows indicate HDAC10-knockdown cells. FIG. 2C is a Western blot of Hela cell cytosol and Hela cell mitochondria, with and without proteinase K (PK) treatment, using three different HDAC10 antibodies (int190, c190 and Novus), a Bcl2 antibody, and a CoxIV antibody.

FIG. 3A is a graph showing the ATP and ADP levels in Hela cells transfected with control siRNA (cKD) or HDAC10-siRNA (HD10-KD), or treated with vehicle (DMSO) or TSA (1 µM for 12 hours). FIG. 3B is a FACS analysis showing the mitochondrial membrane potential of Hela cells transfected with control (cKD) or HDAC10-siRNA (HD10-KD). FIG. 3C is a set of photographs showing the cellular reactive oxygen species (ROS) levels in control (a), HDAC10 knockdown (b) or TSA treated cells (c). Fluorescence indicates ROS accumulation.

FIG. 4A is a set of transmission electron micrographs of control cells (a) and HDAC10 knockdown cells (b). Magnification: 1800×. FIG. 4B is a set of photographs showing cells transfected with HDAC10-siRNA and immunostained with anti-LC3 (a) and anti-HDAC10 (b) antibodies. FIG. 4C is a Western blot of control (cKD) and HDAC10 knockdown cells (HD10-KD) using antibodies to phosphorylated AMPK (pAMPK), AMPK, HDAC10, and actin. FIG. 4D is a Western blot showing the LC3 type I and LC3 type II levels in HDAC10 knockdown cells or TSA-treated cells after incubation with or without compound C(CC), as indicated. FIG. 4E is a bar graph showing the percent cell death of Hela cells co-treated with TSA and either 3MA or compound C, as indicated. FIG. 4F is a bar graph showing the percent cell death of control (cKD) or HDAC10 knockdown (HD10 KD) cells after treatment with 3MA or compound C.

FIG. 5A is a Western blot of mitochondria prepared from cells transfected with control siRNA (cKD) or siRNA for HDAC10, using an anti-(lysine 20 acetylated)-VDAC antibody. FIG. 5B is a set of graphs showing cytosolic (left panel) and mitochondrial (right panel) ATP levels in control (cKD) or HDAC10 knockdown (HD10-KD) cells. FIG. 5C is a graph showing the ATP accumulation in mitochondria in Hela cells stably expressing a Neo vector, wild-type VDAC1, or VDAC1-KR mutant after transfection with control (cKD) or HDAC10 siRNA, as indicated. FIG. 5D shows pyruvate uptake by mitochondria in cells stably expressing either Neo vector of VDAC1-KR mutant, and transfected with either control siRNA (cKD) or HDAC10 siRNA (HD10-KD). Panel (a) shows levels of [$^{14}$C]-pyruvate, and panel (b) shows quantification of those levels by a Phosphor Imager.

FIG. 7A is a set of photographs showing immunostaining of cells treated with either TSA or SAHA, using anti-LC3 antibodies. FIG. 7B is a Western blot showing levels of LC3-type I, LCS-type II, acetylated α-tubulin (AcK-Tub), and acetylated histone (AcK-Histone) in A549 and Hela cells after treatment with DMSO (NT), TSA or SAHA.

DETAILED DESCRIPTION

Figure 1:
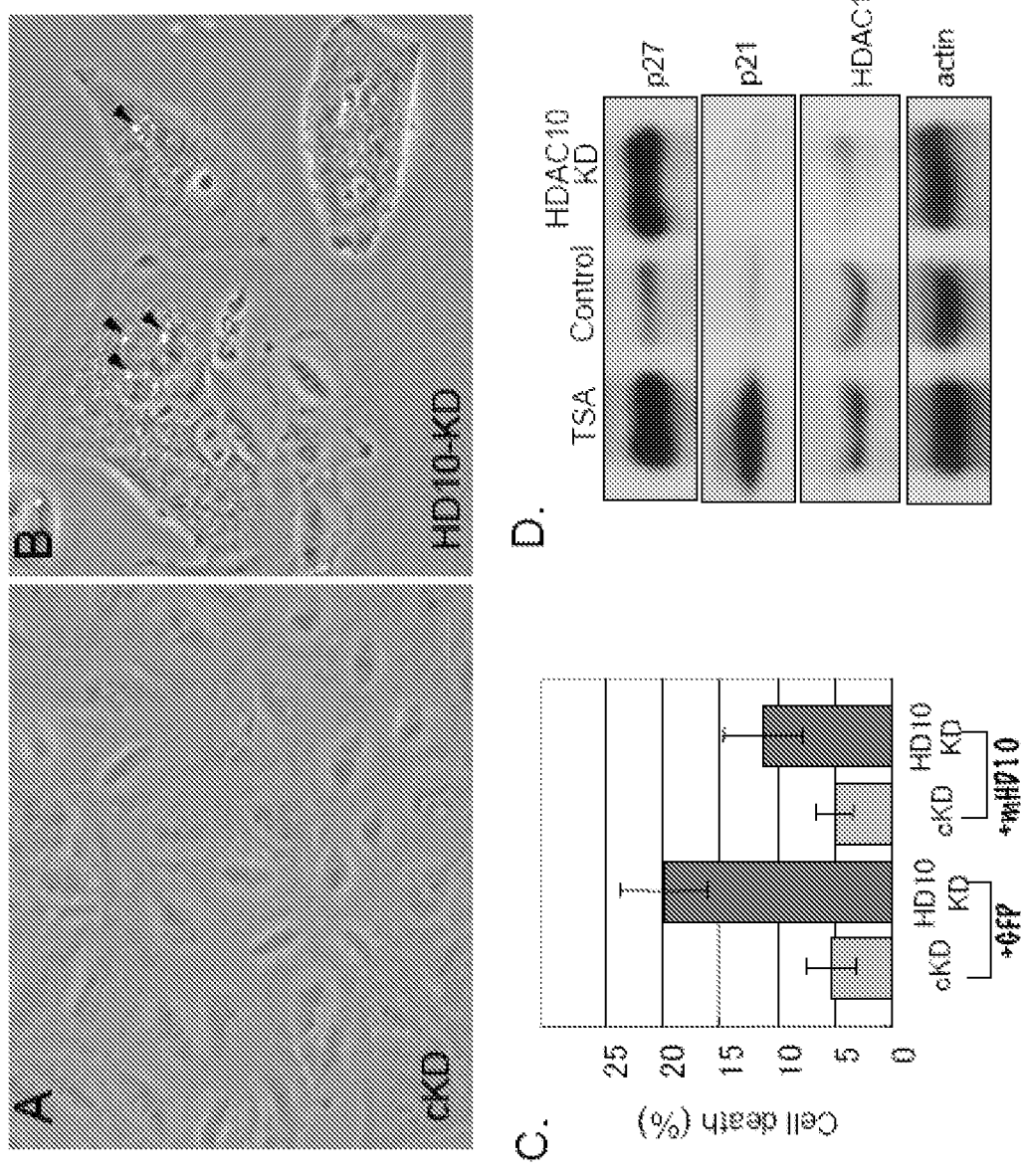
FIG. 1 shows that HDAC10 knockdown causes growth arrest and cell death.

We have found that HDAC10, a type II histone deacetylase, is localized to mitochondria, in contrast to previous reports showing cytosolic and nuclear localization. Inactivation of HDAC10 leads to profound mitochondrial defects accompanied by growth inhibition and severe metabolic stress, supporting a regulatory role of HDAC10 in mitochondrial function. We have identified a mitochondrial substrate for HDAC10: voltage dependent ion channel 1 (VDAC1), a key regulator of mitochondrial metabolite transport across outer membrane and tumor cell survival. We found that HDAC10 controls VDAC1 acetylation, which in turn regulates VDAC1 permeability to certain mitochondrial metabolites. Moreover, we found that pan HDAC inhibitor (pan HDACI) treatment can recapitulate mitochondrial and metabolic phenotypes induced by HDAC10-specific inhibition, implicating the mitochondrion as a major therapeutic target of pan HDACIs. We demonstrate regulation of mitochondria by reversible VDAC1 acetylation and identify mitochondrial perturbation and metabolic stress as integral parts of the anti-proliferative activity of HDAC10 inhibitors. Our results indicate that AMPK and autophagy are activated as part of the metabolic adaptation to energy and metabolic crisis caused by HDACI treatment and HDAC10 inactivation. Thus, combining an HDAC10 inhibitor with agents that inhibit AMPK or autophagy could create a more potent therapy to induce tumor cell death.

As used herein, the term "HDAC10 inhibitor" includes pan HDAC inhibitors (e.g., HDAC inhibitors that inhibit at least class I and class II HDACs), type II HDAC inhibitors (also referred to as "class II HDAC inhibitors"), and HDAC10-specific inhibitors. Certain exemplary HDAC10 inhibitors include, but are not limited to, hydroxamic acid based HDAC inhibitors, including but not limited to, trichostatin A (TSA); hydroxamic acids, including, but not limited to, SAHA, PXD101, NVP-LAQ824, and LBH589; scriptaid; m-carboxycinnamic acid bishydroxamic acid (CBHA); ABHA;

pyroxamide; propenamides; oxamflatin; 6-(3-Chlorophenylureido) caproic hydroxamic acid (3-Cl-UCHA); A-161906; jnj16241199; tubacin and tubacin analogs; small interfering RNA (siRNA); short chain fatty acid HDAC inhibitors; butyrate; phenylbutyrate; hydroxamic acid; trichostatins; epoxyketone-containing cyclic tetrapeptides; HC-toxin; chlamydocin; diheteropeptide; WF-3161; Cyl-1; Cyl-2; non-epoxyketone-containing cyclic tetrapeptides; apicidin; cyclic-hydroxamic-acid-containing peptides (CHAPS); benzamides and benzamide analogs; CI-994; trapoxin; deprudecin; and organosulfur compounds. Certain exemplary siRNA HDAC10 inhibitors include, but are not limited to, siRNAs comprising a sequence selected from SEQ ID NO: 1, SEQ ID NO:2, and SEQ ID NO:3.

Methods of inhibiting cancer cell growth and methods of screening for HDAC10 inhibitors are provided herein. The methods of inhibiting cancer cell growth include contacting a cell with at least one HDAC10 inhibitor in combination with at least one second inhibitor in an amount effective to inhibit cancer cell growth.

The at least one second inhibitor may be an autophagy inhibitor, an AMPK inhibitor, and/or methyl pyruvate (MP). In certain embodiments, the combination of an HDAC10 inhibitor and at least one second inhibitor results in at least an additive inhibition of cell growth. In certain embodiments, the combination results in a synergistic inhibition of cell growth. Certain exemplary autophagy inhibitors include, but are not limited to, chloroquine and 3-methyladenine (3MA). Certain exemplary AMPK inhibitors include, but are not limited to, Compound C.

In certain embodiments, methods of inhibiting cancer cell growth by contacting a cell with an HDAC10 specific inhibitor are provided. HDAC10 specific inhibitors include inhibitory RNAs, such as siRNAs and antisense RNAs. Exemplary siRNAs include siRNAs comprising a nucleotide sequence selected from SEQ ID NOs: 1 to 3. An HDAC10 specific inhibitor is an inhibitor that inhibits HDAC10 more effectively than it inhibits at least one other type II HDAC, such as HDAC4 or HDAC6. In various embodiments, an HDAC10 specific inhibitor inhibits HDAC10 two, five, or ten fold more effectively than it inhibits another type II HDAC. Certain exemplary methods of assaying for HDAC10 activity include, but are not limited to, those methods disclosed herein, such as screening for VDAC acetylation, e.g., as described in the Examples. Certain methods of assessing the activity of certain other HDACs, including HDAC4 and HDAC6, are available to those skilled in the art.

Inhibition of cancer cell growth includes, but is not limited to, inhibition of cancer cell growth as compared to the growth of untreated or mock treated cells, inhibition of metastases, induction of cancer cell senescence, induction of cancer cell death, and reduction of tumor size. In certain embodiments, when a combination of two or more agents is used in the methods described herein, the inhibition of cell growth is additive. In certain embodiments, the inhibition of cell growth is synergistic. The cells may be contacted in vivo, in vitro or ex vivo. The cell may be contacted within a subject, and such contact may result in treatment of cancer in the subject. Suitable subjects are mammals, including humans. The term "contacting," as used herein, includes both directly contacting cells, for example, in vitro, or indirectly contacting cells, such as, for example, by administering an agent to a subject. Further, "contacting" a cell with an agent includes administering or applying a prodrug version of the agent.

Treatment of cancer includes, but is not limited to, reduction in cancer growth or tumor burden, induction of cancer cell senescence, induction of apoptosis of cancer cells, induction of cancer cell death, inhibition of angiogenesis, enhancement of cancer cell apoptosis, and inhibition of metastases. Administration of an effective amount of a therapeutic agent, such as an HDAC10 inhibitor, an autophagy inhibitor, a AMPK inhibitor and/or MP, to a subject may be carried out by any suitable means known in the art including, but not limited to, intraperitoneal, intravenous, intramuscular, subcutaneous, transcutaneous, oral, nasopharyngeal or transmucosal absorption. The specific dose administered in any given case can be adjusted in accordance with the specific cancer being treated, the condition, including the age and weight, of the subject, and other relevant medical factors known to those of skill in the art. Further, one skilled in the art can select appropriate formulation components, such as carriers, buffers, adjuvants, etc., according to the route of administration and/or the subject being treated.

The cancer cell may be from any cancer, including, but not limited to, breast, prostrate, lung, brain, head and neck, liver, pancreatic, kidney, skin, bone, blood, leukemia, lymphoma, ovarian, testicular, and colon cancers. Those cancers which have an apoptosis deficiency may, in certain embodiments, be particularly susceptible to growth inhibition by the methods described herein. Cancers with apoptosis deficiencies include, but are not limited to, cancers with defects in apoptosis regulatory genes or cancers lacking genes involved in stimulating apoptosis.

In certain embodiments, methods of identifying HDAC10 inhibitors are provided. As demonstrated in the Examples, HDAC10 deacetylates VDAC1 and deacetylation of VDAC1 results in effective transport of pyruvate and ATP across the mitochondrial membrane. Lysine 20 of VDAC1 was identified as an acetylation target of HDAC10. Lysine 20 is conserved in VDAC1, VDAC2, and VDAC3. Accordingly, in certain embodiments, HDAC10 is capable of deacetylating VDAC1, VDAC2, and VDAC3. Therefore, in certain embodiments, identifying HDAC10 specific inhibitors includes contacting cells with a test agent and comparing the level of acetylation of a VDAC in the contacted cells to the level of a VDAC acetylation in untreated or mock treated control cells. A test agent effective to inhibit HDAC10 will result in increased acetylation of VDAC as compared to control cells. Alternatively, in certain embodiments, the level of VDAC acetylation may be assessed by assessing the transport of pyruvate and/or ATP across the mitochondrial membrane, e.g., as described in the Examples. HDAC10 inhibitors result in increased ATP in the mitochondria and decreased cytosolic ATP. HDAC10 inhibitors also increase the accumulation of pyruvate in the cytosol and decrease the level of pyruvate in the mitochondria.

In various embodiments, the cells may be contacted with the test agent in vitro, in vivo, or ex vivo. The cells may be from a subject. The subject may be a mammal and suitably the cells are human cells or human cancer cells. Those skilled in the art will appreciate that any cancer cell may be used in the methods described herein. In certain embodiments, the cancer cells are apoptosis deficient. Such apoptosis deficient cells may be, in certain embodiments, cells that overexpress bcl2.

In certain embodiments, methods of treating individuals with cancer using at least one HDAC10 specific inhibitor are provided. Exemplary HDAC10 specific inhibitors include inhibitory RNAs, such as, for example, siRNAs. Certain exemplary siRNAs comprise a sequence selected from SEQ ID NOs: 1 to 3. Further, the screening methods provided herein may be used to identify additional HDAC10 specific inhibitors. In certain embodiments, HDAC10 comprises an amino acid sequence as set forth in SEQ ID NO: 5. An exemplary nucleotide sequence that encodes the amino acid sequence as set forth in SEQ ID NO: 4 is shown in SEQ ID NO: 6.

In certain embodiments, methods of treating individuals with cancer using at least one HDAC10 inhibitor and at least one second inhibitor selected from an autophagy inhibitor, an AMPK inhibitor, and methyl pyruvate are provided.

Those skilled in the art will appreciate that the inhibitors described herein can be administered in a variety of ways to the individual and that dosages will depend on factors such as the type of illness, weight and age of the individual, etc. In certain embodiments, HDAC10 inhibitors, including HDAC10 specific inhibitors, may be administered in combination with at least one second inhibitor such as an autophagy inhibitor, an AMPK inhibitor, or methyl pyruvate. The HDAC10 inhibitors and the second inhibitors may be administered in combination or concurrently as two separate preparations. The HDAC10 inhibitor may also be administered before or after the second inhibitor.

Dose packs comprising a first dosage comprising an HDAC10 inhibitor and a second dosage comprising a second inhibitor selected from an autophagy inhibitor, an AMPK inhibitor, or methyl pyruvate are also provided. In certain embodiments, the dosages contained in such dose packs are suitable for a single administration to a subject. In certain embodiments, a dosage pack comprises multiple single doses of each inhibitor. In certain such embodiments, the multiple single doses are packaged individually.

Each of the references cited herein is incorporated by reference in its entirety. The following examples are meant to be illustrative and are not meant to limit the scope of the invention.

EXAMPLES

Example 1

Materials and Methods

Cell Lines, siRNA Transfection and Cell Death Assay

Cells were maintained in 10% FBS containing DMEM (GIBCO). In most experiments involving HDAC10 knockdown, cell lines were transiently transfected with stealth siRNA for GFP (CCGACCACAUGAAGCAGCAC-GACUU; SEQ ID NO: 4) as a control, HDAC10 (#1, UCCA-GUGUGUAAGGCAGCUGCAUCU, SEQ ID NO: 1; #2, UGCGCCGUUAGUAAACAUCGCUCAA, SEQ ID NO: 2; or #3, CGGGUUCUGUGUGUUCAAC, SEQ ID NO: 3). In the experiments shown in FIGS. 1A, 1B, 4A(a), and 4A(b), cells were infected with retrovirus expressing siRNA #1, #2, or #2.

Various cell lines were treated with TSA (Sigma), Compound C (Calbiochem), or 3MA (3-methyl adenine; Sigma). Cell death was measured using CytoTox96 Non-Radioactive Cytotoxicity Assay (Promega). VDAC1-KR mutant was generated by converting all acetylated lysine, K20, K28, K61 and K224 (Kim et al., 2006) to arginine by site directed mutagenesis. The wild type or VDAC1-KR mutant was stably transduced into Hela cells by retrovirus-mediated gene transfer.

Antibodies and Plasmids

Antibodies against HDAC10 were produced by injecting rabbits with recombinant protein against a.a. 367-557 (Int-190) or a.a. 480-669 (C-190) followed by affinity purification. Additional HDAC10 antibodies were purchased from Novus, Biovision and Abcam. Acetylated VDAC1-specific antibody was produced by injecting a VDAC1 peptide antigen with lysine 20 acetylated followed by two-step affinity-purification using both non-acetylated and acetylated peptide columns as described previously (Ito et al., 2002). Acetylated VDAC was detected in purified mitochondrial fractions. Other antibodies were from Cell Signaling Technology (VDAC1, Bcl2, phospho-AMPK, AMPK), Sigma (actin and acetylated-alpha-tubulin) and BioReagents (mitochondrial-Hsp70).

Immunostaining

Immunostaining was performed essentially as described previously (Hubbert et al. (2002) *Nature* 417: 455-458). Specifically, cells were cultured on glass coverslips with or without MitoTracker Red CMXRos (Molecular Probes) followed by fixation in 4% paraformaldehyde in PBS for 15 min at room temperature. In cellular ROS detection, cells were incubated with CM-$H_2$DCFDA (Molecular Probes), washed with PBS and subjected to microscopy. Cells were examined on a Zeiss Axio Imager wide field fluorescence microscope equipped with an Orca ER monochrome cooled-CCD camera using a 60×/1.4-numerical-aperture oil objective. For mitochondrial membrane potential detection, cells were stained with JC-1 (Molecular Probes) and analyzed by FACSCaliber (BD) with excitation at 488 nm and emission at 590 nm.

Mitochondria Analysis

Subcellular fractionation and mitochondria purification were performed as described (Schwer et al. (2002) *J. Cell Biol* 158: 647-657). In brief, cells were homogenized in ice-cold buffer H (210 mM Mannitol, 70 mM sucrose, 0.1 mM EGTA, 2 mM HEPES-KOH, 0.5 mg/ml BSA, pH 7.5). The homogenate was centrifuged twice at 500 g to remove nuclei and unbroken cells. Mitochondria were sedimented by centrifugation at 9,000 g for 15 min, washed twice with buffer H, and resuspended in Uptake buffer (55 mM Mannitol, 24 mM sucrose, 10 mM $KH_2PO_4$, 90 mM KCl, 50 mM Malic acid, 10 mM Tris-HCl, pH 7.2, 280 mOsm).

Cellular, cytosolic or mitochondrial ATP levels or ADP levels were measured using ATP Bioluminescence Assay Kit HS II (Roche). Pyruvate transport assay was modified from Duerr's method (Duerr et al. (1993) *Compar Biochem Physiol* 106: 889-893). Briefly, purified mitochondria were incubated with [$^{14}$C]-pyruvate in the mitochondria-uptake buffer supplied with 2 mM ADP at 37° C. for 20 minutes. After incubation, mitochondria were diluted by Uptake buffer and collected to nitrocellulose membrane (0.8 μm pore). [$^{14}$C]-pyruvate uptake levels were measured by Phosphor Imager after exposing nitrocellulose membrane to Phosphor screen (Amersham).

VDAC1 permeability assay was performed as described (Colombini (2007) *Meth Cell Biol* 80: 241-260). Briefly, isolated mitochondria were supplied with ADP in reaction buffer (0.3M Sucrose, 5 mM HEPES, 1 mM EGTA, 1 mM $MgCl_2$, 2 mM $KH_2PO_4$, 0.1% BSA, PH 7.5, supplied with 10 mM Glucose, 0.2 mM NADP, 0.2 mM KCN and 20 mg/ml Atractylosides, and an enzyme mix containing Hexokinase and Glucose-6-phosphate dehydrogenase). ATP produced by the inter-membrane space enzyme adenylate kinase, and exported via the VDAC1, was coupled in the reaction buffer to generate NADPH, which is recorded by spectrophotometer absorption at 340 nm.

Statistical Analysis

Two-tailed Student's t-test was conducted for statistic analysis of quantitative data.

Example 2

HDAC10 Inhibition Causes Growth Arrest and Cell Death

Mitochondrial defects often lead to energy crisis that activates metabolic stress responses controlled by the AMP-activated kinase (AMPK). In cells under metabolic stress, activated AMPK induces prominent metabolic adaptations including autophagy, which by digesting cellular contents supplies ATP and fuels to sustain cell survival (Towler et al. (2007) *Circ Res* 100: 328-341). As part of the metabolic checkpoint, AMPK also stabilizes the cdk inhibitor p27 leading to growth arrest (Liang et al. (2007) *Nat Cell Biol* 9, 218-224).

To investigate whether inhibition of HDAC10 expression results in mitochondrial defects and metabolic stress responses, possibly leading to growth arrest and cell death, A549 cells were infected with retrovirus expressing control or HDAC10-specific siRNA, as described in the Materials and Methods. We found that the expression of three different HDAC10-siRNAs all led to prominent growth arrest (FIG. 1A-B) as well as some non-apoptotic cell death (~20%). We obtained the same result in U2OS cells (data not shown). As evident in FIG. 1, the control virus infected cells grew to confluency, while the HDAC10-siRNA infected cells stopped proliferating and showed prominent vacuoles. To demonstrate that these effects were a result of the HDAC10-specific siRNAs, Hela cells were co-transfected with either a control siRNA or an HDAC10 siRNA, and with either a vector expressing GFP, or a vector expressing a mouse HDAC10 that would be expected to be resistant to the HDAC10 siRNA. Cell death was measured after 72 hours using an LDH cytotoxicity assay (Promega CytoTox-96). As shown in FIG. 1C, expression of the siRNA-resistant mouse HDAC10 appears to reverse the effects of the HDAC10 siRNA, resulting in less cell death.

Figure 13:
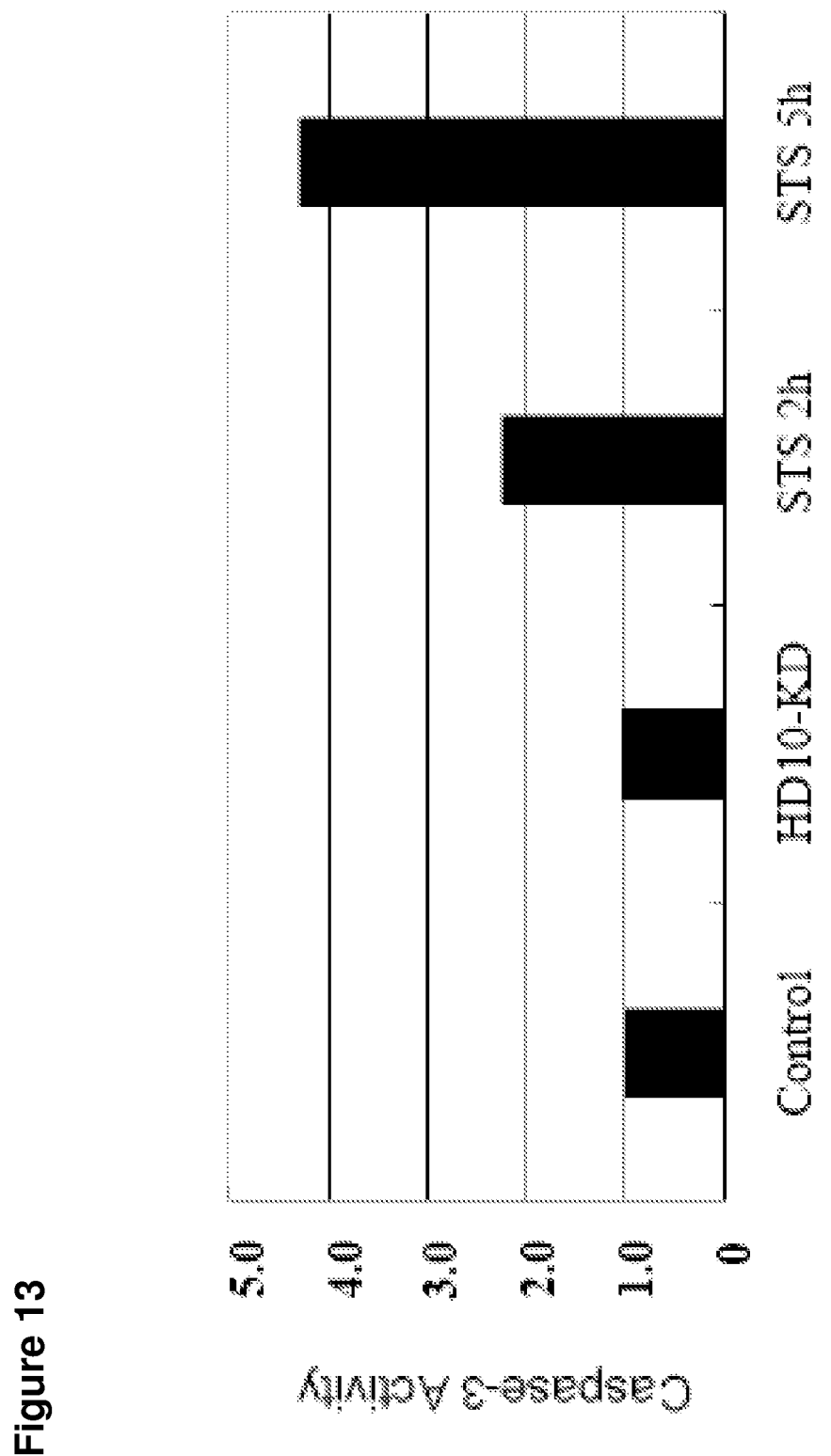
FIG. 13 shows that HDAC10 inactivation leads to non-apoptotic cell death. Caspase-3 activity was measured in Hela cells transfected with control siRNA or HDAC10 siRNA, or treated with staurosporin (STS) for 2 hours or 5 hours.

To determine if the observed cell death was through apoptotic or non-apoptotic processes, caspase-3 activity were measured in Hela cells transfected with control siRNA or HDAC10 siRNA, using the Caspase-3 Activity Assay (BIOMOL International) 3 days after transfection. As shown in FIG. 13, HDAC10 inactivation appears to lead to non-apoptotic cell death. As a positive control, Hela cells were incubated with 2 µM staurosporin (STS) for 2 hours or 5 hours. STS led to apoptotic cell death in that assay, as indicated by the increase in Caspase-3 activity in FIG. 13.

P27, p21, and HDAC10 levels were then determined in Hela cells after treatment with trichostatin A (TSA) (1 µM for 16 hours) or an HDAC10 siRNA by Western blot. As shown in FIG. 1D, in growth arrested HDAC10 knockdown cells, p27 but not p21 levels were greatly elevated, suggesting an activation of the metabolic checkpoint. Actin is shown as a control. Consistent with previous reports, treatment with the pan HDAC inhibitor Trichostatin A (TSA), which inhibits HDAC10 and other HDAC members, led to induction of both p21 and p27 (FIG. 1D). These results indicate that HDAC10 inhibition mediates a subset of biological effects of HDACI involving p27, whose induction has been linked to metabolic stress response (Liang et al. (2007) *Nat Cell Biol* 9, 218-224).

Example 3

HDAC10 Localizes to the Mitochondrial Outer Membrane

Figure 2:
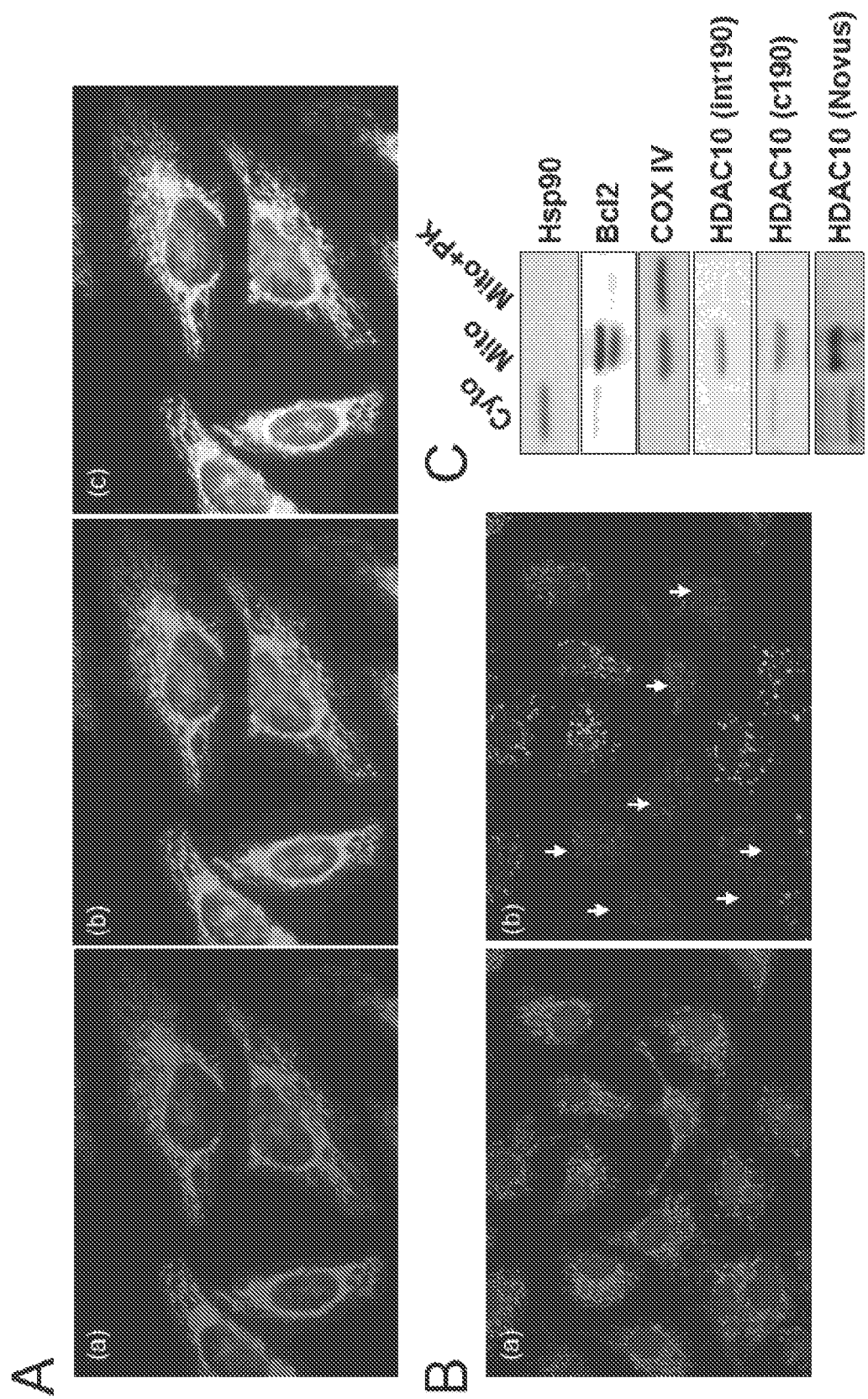
FIG. 2 demonstrates that HDAC10 localizes on mitochondrial outer membrane.
Figure 6:
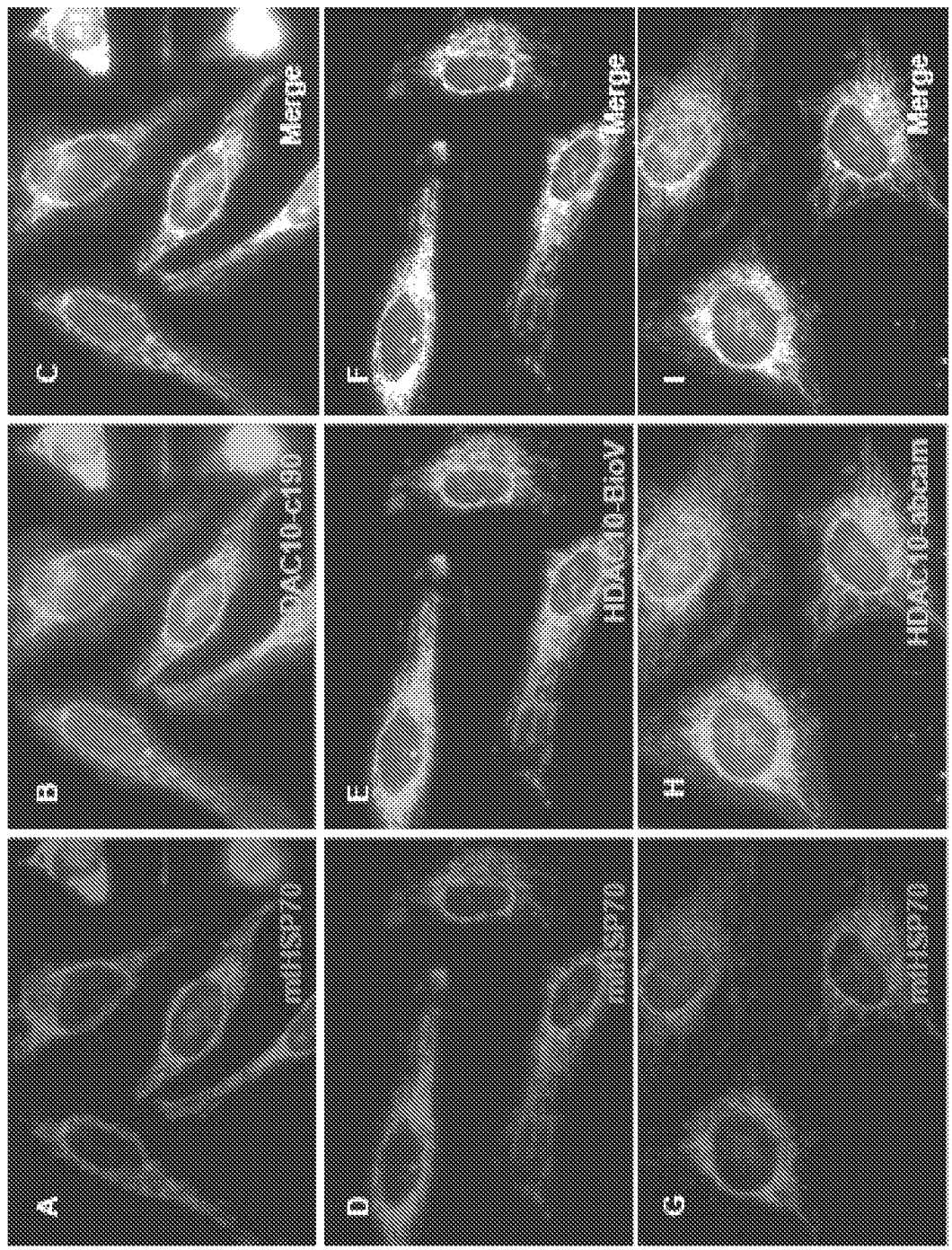
FIG. 6 is a set of photographs showing the mitochondria localization pattern of HDAC10 using three HDAC10-specific antibodies. Panels (A), (D), and (G) show immunostaining with an antibody to a mitochondrial-localized protein, mtHSP70. Panels (B), (E), and (H) show immunostaining with three different antibodies to HDAC10. Panels (C), (F), and (I) show a merge of the two previous staining patterns.

To characterize how HDAC10 regulates proliferation, specific antibodies for HDAC10 were generated and the subcellular localization of HDAC10 in Hela cells was determined by immunostaining. Although ectopically expressed HDAC10 was previously reported to reside mostly in cytosol and occasionally in the nucleus, in our experiments, immunolocalization analyses showed that endogenous HDAC10 is concentrated at mitochondria (FIG. 2A(a)), as shown by its extensive co-localization with mitochondrial Hsp70 (FIG. 2A(b)). Cellular nuclei were stained with Hoechst 33342, and are shown in FIG. 2A(c). A similar mitochondrial localization pattern was obtained by three additional HDAC10-specific antibodies (see FIG. 6). To confirm that the antibodies were detecting endogenous HDAC10, A549 cells were transfected with an siRNA for HDAC10. After 72 hours, cells were treated with MitoTracker Red CMXRos to detect mitochondria and then fixed and immunostained with an anti-HDAC10 antibody (int190). FIG. 2B shows that the mitochondrial staining of HDAC10 was greatly reduced upon transfection of an HDAC10-siRNA (see panel (b), arrows). Panel (a) shows mitochondria detected with MitoTracker Red CMXRos. These results confirm that the immunostaining assay is detecting HDAC10 in the mitochondria because inhibition of HDAC10 protein expression using an siRNA to HDAC10 results in a decrease in signal.

Finally, cytosol and mitochondria from Hela cells were fractionated and the fractions subjected to immunoblotting using three different HDAC10 antibodies (int190, c190 and Novus), as well as antibodies against outer-membrane associated Bcl2 and matrix localized CoxIV. The results are shown in FIG. 2C (lanes 1 and 2). All three HDAC10 antibodies detected HDAC10 in the mitochondrial fraction, demonstrating that HDAC10 is concentrated at mitochondria. To determine the specific mitochondrial compartment to which HDAC10 is localized, we treated purified mitochondria with proteinase K (20 µg/ml for 20 minutes), which degrades outer membrane associated proteins but not matrix-localized proteins. As shown in FIG. 2C (lane 3), proteinase K treatment led to complete degradation of mitochondrial HDAC10 while preserving matrix protein COXIV. We conclude that HDAC10 is a mitochondrial outer membrane-associated deacetylase.

Example 4

HDAC10 Knockdown Leads to Mitochondrial Dysfunction

The mitochondria localization of HDAC10 prompted an investigation into whether HDAC10 is required for mitochondria function. Hela cells were transfected with control siRNA (cKD) or an HDAC10-siRNA (HD10-KD), or treated with vehicle (DMSO) or TSA (1 µM for 12 hours). ATP levels were determined using a luciferase-based ATP assay. ADP levels were measured using the same assay after converting ADP to ATP. ATP levels are shown as nMole/mg of total protein, and data are represented as mean+/−standard deviation in FIG. 3A. In this experiment, both siRNA knockdown of HDAC10 (HD10-KD) and TSA treatment led to a marked reduction in cellular ATP levels.

Figure 3:
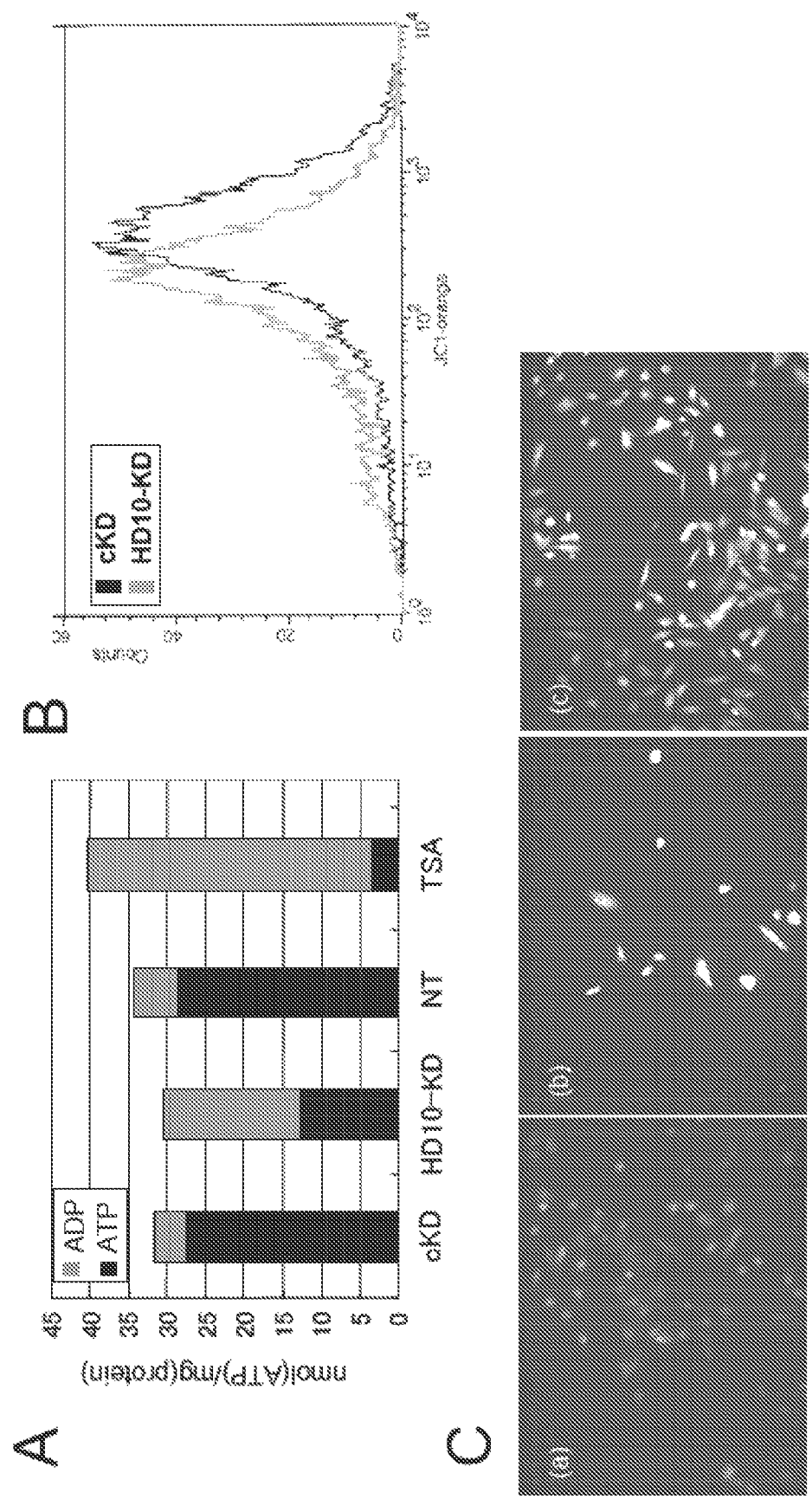
FIG. 3 demonstrates that HDAC10 knockdown causes mitochondrial defects.

The membrane potential of Hela cells transfected with control siRNA (cKD) or an HDAC10-siRNA (HD10-KD) was then determined by FACS analysis using JC-1 staining. As shown in FIG. 3B, mitochondria transmembrane potential decreased in cells transfected with HDAC10-siRNA. Finally, the cellular reactive oxygen species (ROS) level was determined in Hela cells transected with an HDAC10 siRNA, control cells transfected with a control siRNA, and in cells treated with TSA (1 µM for 12 hours), using ROS-sensitive $H_2DCFDA$ fluorescence (Molecular Probes). In that assay, fluorescence indicates ROS accumulation. The results of that experiment are shown in FIG. 3C, which shows the accumulation of reactive oxygen species in HDAC10 knockdown cells and cells treated with TSA (panels (b) and (c), respectively). The decrease in cellular ATP levels, the decrease in mitochondrial transmembrane potential, and the accumulation of reactive oxygen species are all hallmarks of mitochondria dysfunction. Thus, our experiments demonstrate that inactivation of HDAC10 leads to mitochondria defects.

Example 5

HDAC10 Knockdown Induces Autophagy Via AMPK Activation

Figure 4:
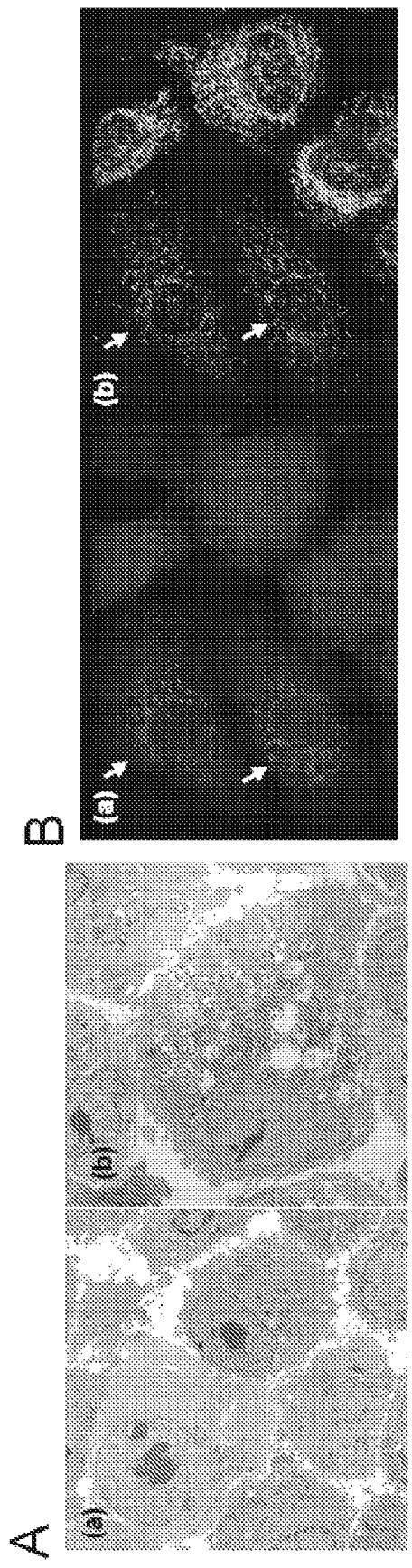
FIG. 4 demonstrates that HDAC10 knockdown induces autophagy via AMPK activation.
Figure 4:
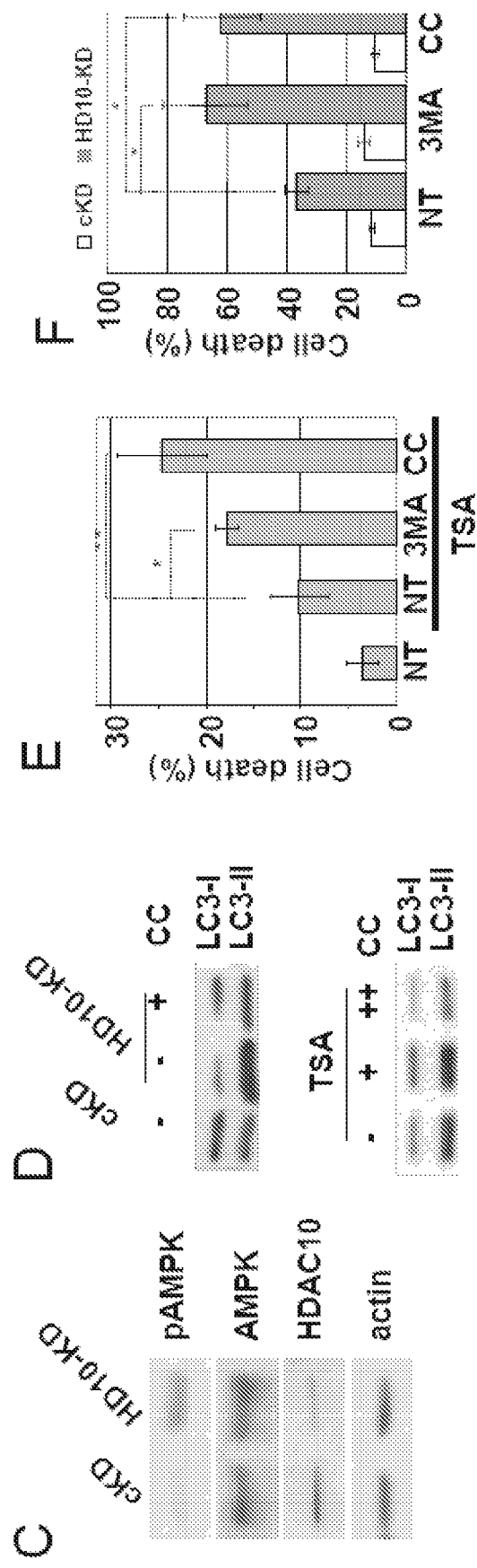

In arrested HDAC10 knockdown cells, we also observed prominent vacuoles in the cytoplasm (FIG. 1B, arrowheads). To understand the nature of this phenotype, we performed transmission electron microscopy (EM) on A549 cells transfected with control siRNA or HDAC10 siRNA. As shown in FIG. 4A, the EM analysis revealed a dramatic accumulation of autophagosome- and autolysosome-like structures in HDAC10 knockdown cells ((b), compare to control cells (a)), indicating that autophagy is activated upon loss of HDAC10. To confirm this conclusion, Hela cells were transfected with HDAC10 siRNA and then immunostained with anti-LC3 and anti-HDAC10 antibodies. While LC3 type I is cytosolic, type II associates with autophagosomes. As shown in FIG. 4B, prominent induction of LC3 (ATG8)-positive autophagic vesicles and the conversion of the cytosolic form of LC3-I to the autophagosome-associated LC3-II were readily observed in HDAC10 knockdown cells (arrows). FIG. 4D is a Western blot showing the LC3 type I and LC3 type II levels in HDAC10 knockdown cells or TSA-treated (1 µM for 12 hours) cells after incubation with or without AMPK inhibitor, compound C(CC; +=2 µM and ++=10 µM). Hela cells were used for this experiment. Data are represented as mean+/−standard deviation. Differences with untreated samples were significant for *p<0.05. Together, these results demonstrate that the inactivation of HDAC10 leads to autophagy induction even under normal nutrient conditions.

To further evaluate whether the metabolic stress response is indeed activated in HDAC10 knockdown cells, we assessed AMPK status by determining AMPK phosphorylation on threonine 172, which is associated with active forms of the kinase (Hawley et al. (1996) *J Biol Chem* 271, 27879-27887). FIG. 4C is Western blot of cells transfected with control siRNA (cKD) and HDAC10 siRNA, developed using antibodies to phosphorylated AMPK (pAMPK), AMPK, HDAC10, and actin. As shown in that figure, AMPK became phosphorylated in HDAC10 knockdown cells, indicating that it is activated. Interestingly, as noted above, treatment with an AMPK inhibitor, compound C, inhibited autophagy activation in HDAC10 knockdown cells (FIG. 4D). Thus, HDAC10 inactivation results in the activation of AMPK, autophagy and p27, which are three key components of the metabolic stress response. Treatment with AMPTK inhibitor compound C, inhibited these effects. These findings support the conclusion that HDAC10 deficiency causes mitochondria defects, which lead to AMPK-dependent metabolic stress response.

Example 6

HDACI Effects are Similar to HDAC10 siRNA

Figure 7:
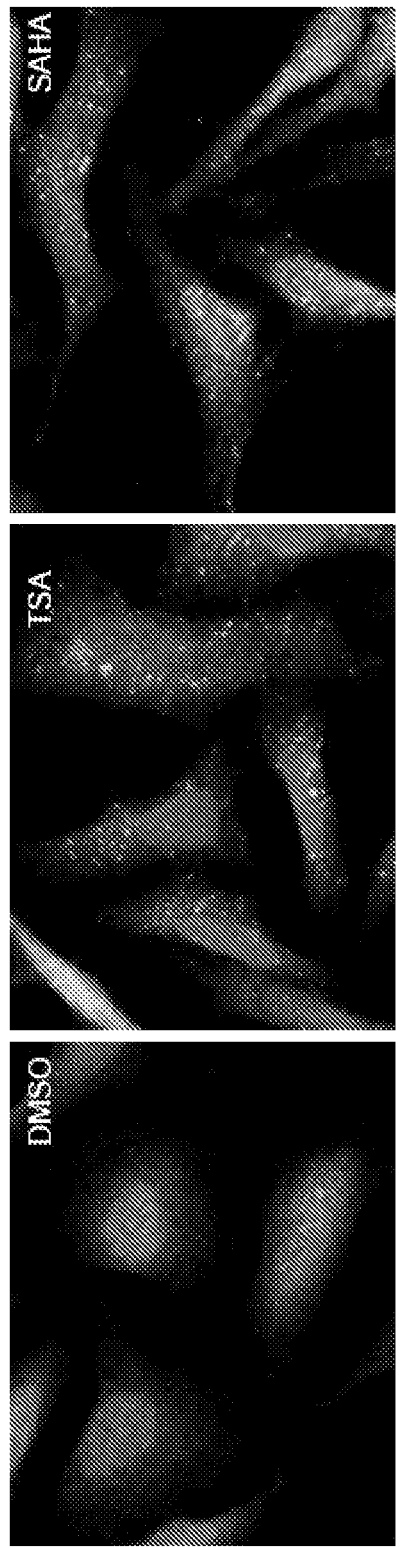
FIG. 7 demonstrates that treatment with the HDACIs TSA or suberoylanilide hydroxamic acid (SAHA) activated AMPK and induced autophagy.
Figure 7:
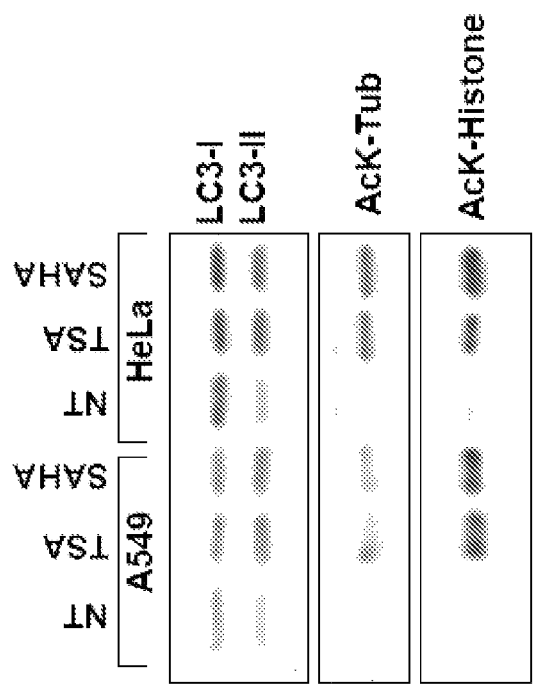

The prominent effects of HDAC10 inactivation on mitochondrial functions prompted us to determine if an HDAC inhibitor (HDACI) would result in similar defects. As shown in FIGS. 3A and 3C, treatment with TSA also led to a reduction in cellular ATP levels and the production of reactive oxygen species (ROS). To investigate whether a pan HDAC inhibitor would have a similar affect, Hela cells were treated for 12 hours with TSA (1 µM), suberoylanilide hydroxamic acid (SAHA) (5 µM), or DMSO as a control. Cells were then fixed and stained with anti-LC3 antibody. As shown in FIG. 7A, cells treated with either TSA or SAHA formed LC3-associated vacuoles. FIG. 7B shows Western blots of A549 and Hela cells treated with DMSO (NT), TSA or SAHA, detected with antibodies to type I LC3, type II LC3, acetylated α-tubulin (AcK-Tub), and acetylated histone (AcK-Histone). These results show that levels of LC3-type II, acetylated α-tubulin, and acetylated histone increase upon TSA and SAHA treatment in A549 and Hela cells. Thus, TSA and SAHA treatment appear to activate AMPK and induce autophagy. Further, as noted above, TSA-induced autophagy is suppressed by compound C treatment (see FIG. 4D). Thus, HDACI treatment also leads to mitochondria defects and metabolic stress.

Example 7

Inhibition of HDAC and AMPK-Autophagy Decreases Cell Survival

We next determined the importance of the AMPK-autophagy activation in the anti-proliferative effects of HDACI. Autophagy induced by HDACI or HDAC10 inactivation could either enhance cell survival by supplying macromolecule and fuel source, or it could promote autophagic cell death. To test these possibilities, Hela cells were co-treated with TSA (0.2 µM for 48 hours) and either AMPK inhibitor compound C (10 µM for 48 hours) or autophagy inhibitor 3 methyladenine (3MA) (10 mM for 24 hours) and then assayed for cell death using the LDH cytotoxicity assay (Promega CytoTox-96). As shown in FIG. 4E, compound C and 3MA treatment both markedly enhanced cell death induced by TSA. Data are represented as mean+/−standard deviation. Differences with untreated samples were significant for **p<0.01 and *p<0.05.

In a second experiment, Hela cells were transfected with control siRNA or HDAC10 siRNA and then treated with 3MA (10 mM for 24 hours) or compound C (10 µM for 24 hours). Cell death was again determined using the LDH cytotoxicity assay. As shown in FIG. 4F, 3MA and compound C treatment increased cell death in HDAC10 knockdown cells. These results support the conclusion that the AMPK-autophagy pathway is activated as part of the metabolic stress response and provides a survival advantage to cancer cells treated with HDACI.

Example 8

HDAC10 Acetylates VDAC

The subcellular localization and phenotypic analysis of HDAC10 deficient cells support a role of HDAC10 in mitochondria. To determine how HDAC10 might regulate mitochondria function, we searched for mitochondrial substrates of HDAC10. The localization of HDAC10 suggests that its substrates are likely outer-membrane-associated mitochondrial proteins. Interestingly, among ~100 putative mitochondrial acetylated proteins (Kim et al. (2006) *Mol Cell* 23, 607-618), the voltage-dependent anion channels (VDAC) are localized to the outer membrane. VDACs are critical channels that control the flow of ions and metabolites, including ATP, across the mitochondria outer membrane (reviewed in Rostovtseva et al., (2005) *J Bioenerg Biomem* 37: 129-142). VDACs have also been implicated in promoting tumor cell survival (Vander Heiden et al. (2000) *Proc Natl Acad Sci USA*

Figure 5:
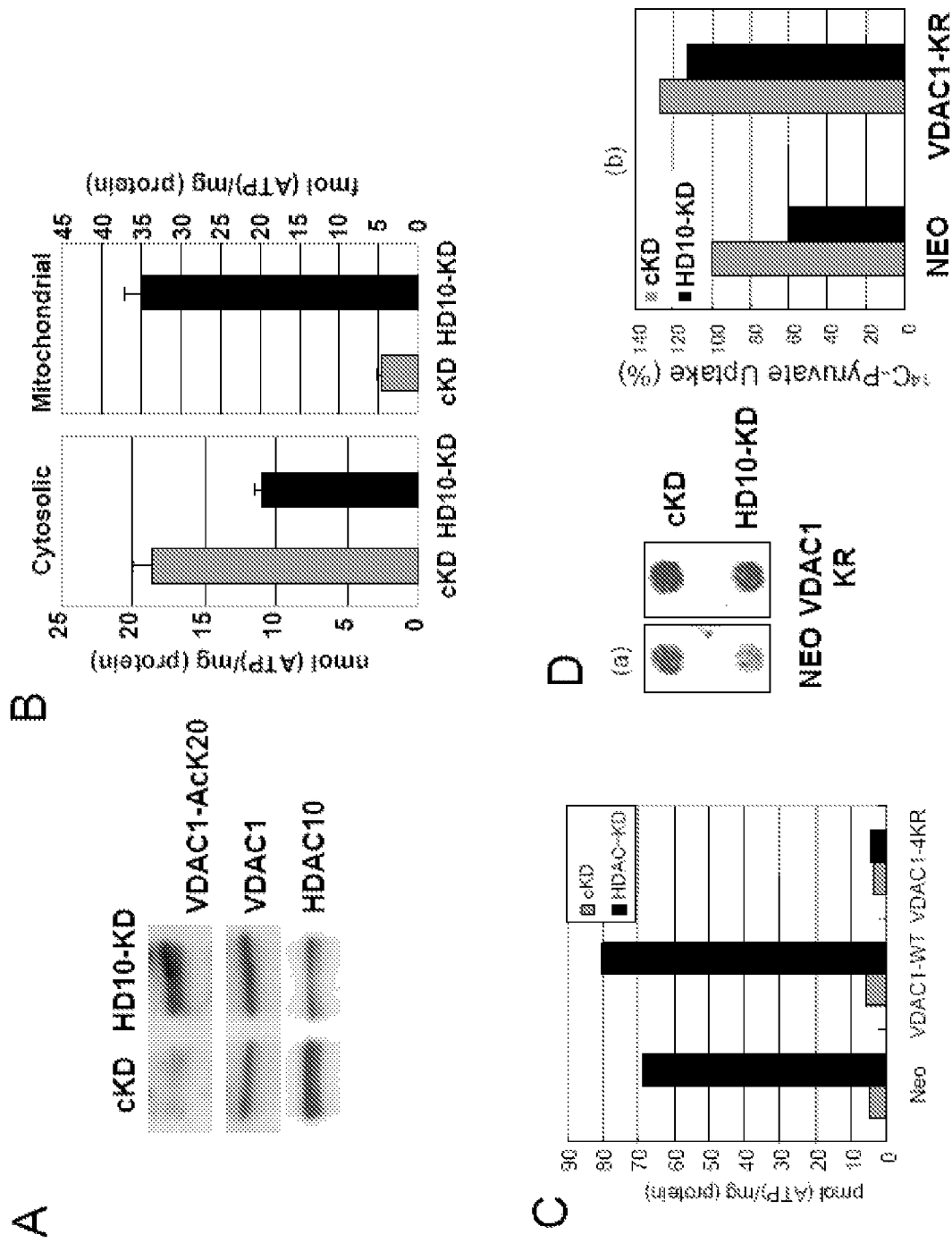
FIG. 5 demonstrates that HDAC10 regulates VDAC1 acetylation and mitochondria metabolite transport.

97: 4666-4671; Yagoda et al. (2007) *Nature* 447: 864-868). Despite their importance, little is known about how VDAC channel permeability is regulated. To determine if VDAC is subject to acetylation regulated by HDAC10, we generated an antibody that specifically recognizes VDAC1 acetylated on lysine 20 (Ac-K20), a position previously shown to be acetylated by mass spectrometry (Kim et al. (2006) *Mol Cell* 23, 607-618). Hela cells were transfected with control siRNA or siRNA for HDAC10. Mitochondria prepared from transfected cells were isolated and separated on a Western blot, then probed using the anti-(lysine 20 acetylated)-VDAC antibody. As shown in FIG. 5A, we found that endogenous VDAC1 becomes hyperacetylated in HDAC10 knockdown cells. This result suggests that HDAC10 is a deacetylase that regulates VDAC1 acetylation.

Example 9

VDAC Function is Regulated by Acetylation

Figure 10:
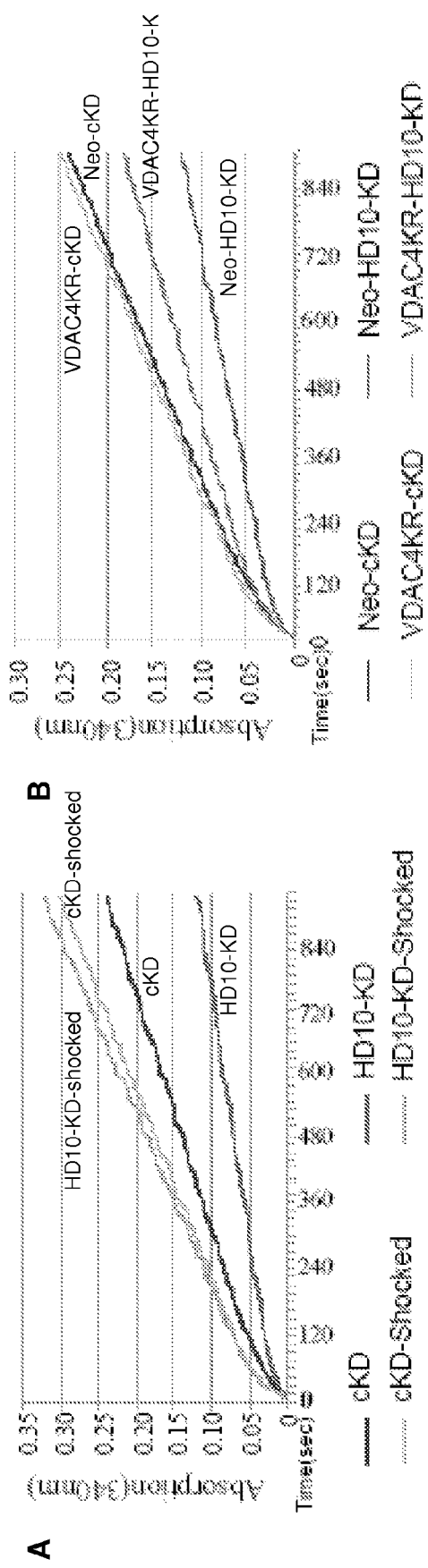
FIG. 10 shows that HDAC10 regulates VDAC1 acetylation and mitochondrial metabolite transport. (A) VDAC1 permeability for ADP/ATP in mitochondria from Hela cells transfected with control-siRNA (cKD) and HDAC10-siRNA (HD10-KD). The top panel shows the rate of ATP export from mitochondria. "Shocked" indicates that the mitochondria were disrupted by incubation with ice-cold water. The bottom panel shows the average ATP transport rate calculated from three independent experiments. (B) VDAC1 permeability for ADP/ATP in mitochondria from Hela cells stably expressing vector (NEO) or VDAC1-KR mutant and transfected with control siRNA or HDAC10-siRNA. The top panel shows the rate of ATP export from mitochondria. "Shocked" indicates that the mitochondria were disrupted by incubation with ice-cold water. The bottom panel shows the average percentage of reduction in permeability induced by HDAC10-siRNA in control (NEO) and VDAC1-KR mutant expressing Hela cells.

VDAC1 lysine 20, one of the residues subject to acetylation, is important in determining VDAC channel gating property (Blachly-Dyson et al., 1990; Yehezkel et al., 2007). Acetylation could, in principle, neutralize the charge of lysine 20 and thereby inhibit the transport of anions and metabolites through the channel. We therefore assessed whether VDAC acetylation affects its channel permeability. To this end, we measured VDAC permeability to ATP in isolated mitochondria purified from Hela cells transfected with control siRNA or transfected with HDAC10 siRNA. The rate of ATP export from mitochondria was plotted by measuring cytosolic ATP-dependent time course production of NADPH (See FIG. 10A, top panel, which shows one representative experiment). mitochondrial outer membranes were disrupted by incubation with ice-cold water (shocked), allowing VDAC1-independent diffusion of ATP into the cytosol. FIG. 10A, bottom panel, shows average ATP transport rate calculated from three independent experiments. Data are represented as mean+/−standard deviation. In that experiment, HDAC10 deficient mitochondria (FIG. 10A, HD10-KD) showed marked reduction in ATP permeability compared to mitochondria purified from control cells (FIG. 10A, cKD). This defect is specific, as the disruption of the mitochondrial outer-membrane by osmotic shock normalized the ATP permeability in control and HDAC10-deficient mitochondria (FIG. 10A, shocked).

To confirm that the effect was VDAC acetylation-dependent, Hela cells stably expressing a Neo vector and Hela cells stably expressing a VDAC1-KR mutant that is resistant to acetylation were transfected with control siRNA or HDAC10-siRNA. VDAC permeability was measured as described above. Data are represented as mean+/−standard deviation. As shown in FIG. 10B, the defect in ATP permeability was markedly reversed in mitochondria stably expressing an acetylation-resistant VDAC1-KR mutant. These findings support a model wherein hyperacetylated VDAC1 caused by HDAC10 inactivation has reduced permeability for ATP.

We then focused on two metabolites, ATP and pyruvate, which use VDAC channels to enter or exit mitochondria. To explore whether HDAC10 is required for efficient VDAC-mediated ATP transport from mitochondria, we measured the concentration of ATP in the mitochondrial and cytosolic compartments. Consistent with the analysis of total cellular ATP (FIG. 3A), cytosolic ATP levels were reduced in HDAC10 knockdown Hela cells compared to cells transfected with control siRNA, as measured by a luciferase-based ATP assay (FIG. 5B, left panel). Data are represented as mean+/−standard deviation. In contrast, mitochondrial ATP levels were significantly higher (~10 fold) in HDAC10 knockdown cells (FIG. 5B, right panel), consistent with an impaired VDAC-dependent export of ATP to the cytosol.

To further assess if VDAC acetylation suppresses ATP export from mitochondria, we generated Hela cell lines stably expressing a Neo vector, wild-type VDAC1, or an acetylation-resistant VDAC1 mutant (KR mutant, see Materials and Methods). Each of the stable Hela cell lines was then transfected with a control siRNA or an HDAC10 siRNA. The results of that experiment are shown in FIG. 5C. Expression of the acetylation-resistant VDAC1-KR mutant effectively reduced the accumulation of ATP in the mitochondria of HDAC10 knockdown cells (FIG. 5C), supporting the conclusion that hyper-acetylated VDACs are less permeable to ATP.

To gain further evidence that VDAC acetylation affects the import of pyruvate into mitochondria, we assessed pyruvate uptake by purified mitochondria in vitro. Mitochondria were purified from Hela cells stably expressing a Neo vector or VDAC1-KR mutant, and then transfected with control siRNA or HDAC10 siRNA. The purified mitochondria were incubated with [$^{14}$C]-pyruvate and assayed as described in Materials and Methods. As shown in FIG. 5D, mitochondria purified from HDAC10 knockdown cells stably expressing the Neo vector had reduced ability to take up pyruvate. Moreover, this defect was reversed in mitochondria that express the acetylation-resistant VDAC1-KR mutant (FIG. 5D). Together, these findings demonstrate that at least VDAC1 activity is regulated by acetylation controlled by HDAC10.

Example 10

Figure 11:
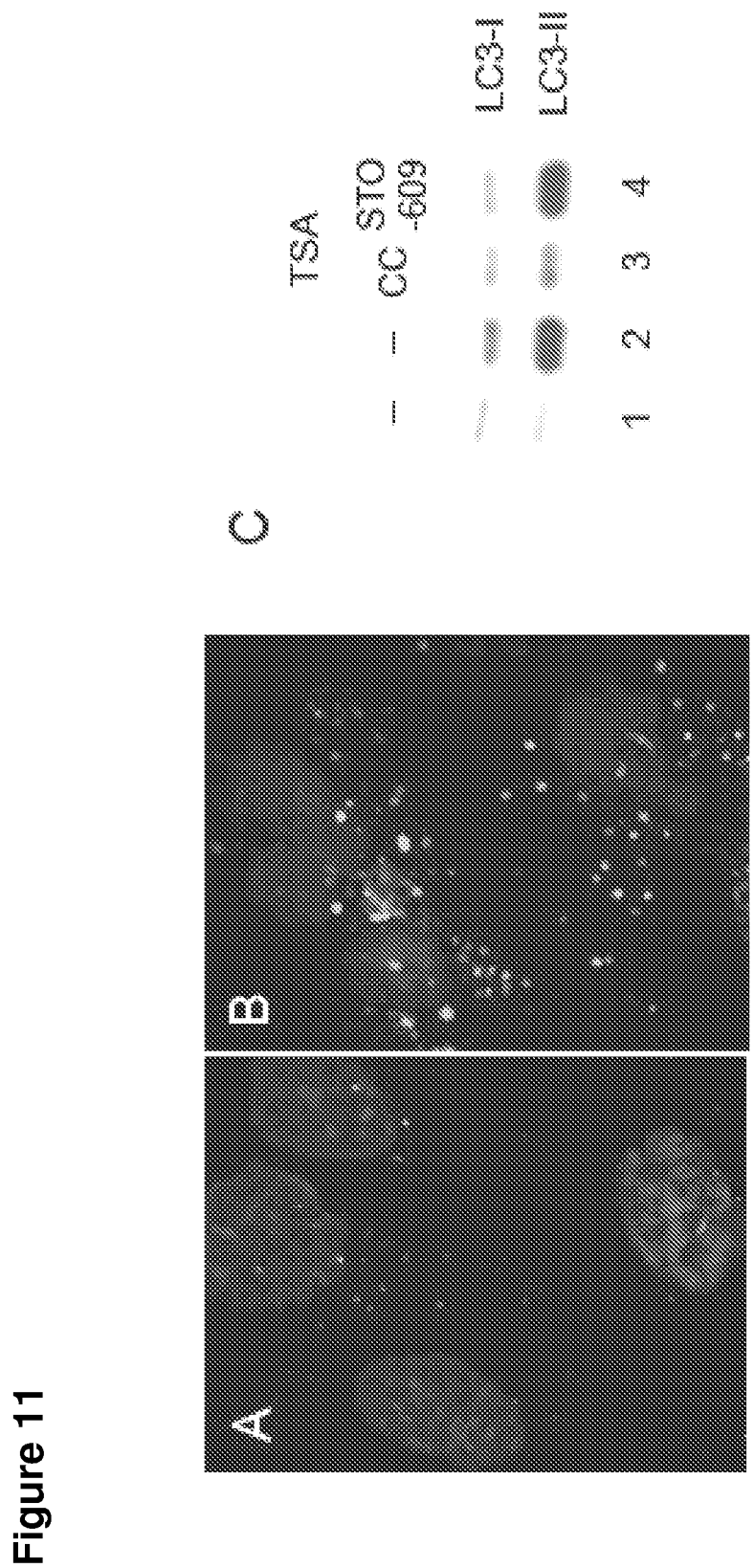
FIG. 11 shows that HDACI treatment activates AMPK-dependent metabolic stress response. (A-B) Autophagy induction in Hela cells treated with vehicle (DMSO, A) or TSA (B). (C) Autophagy induction in untreated or TSA-treated Hela cells incubated with compound C(CC) or STO-609.
Figure 12:
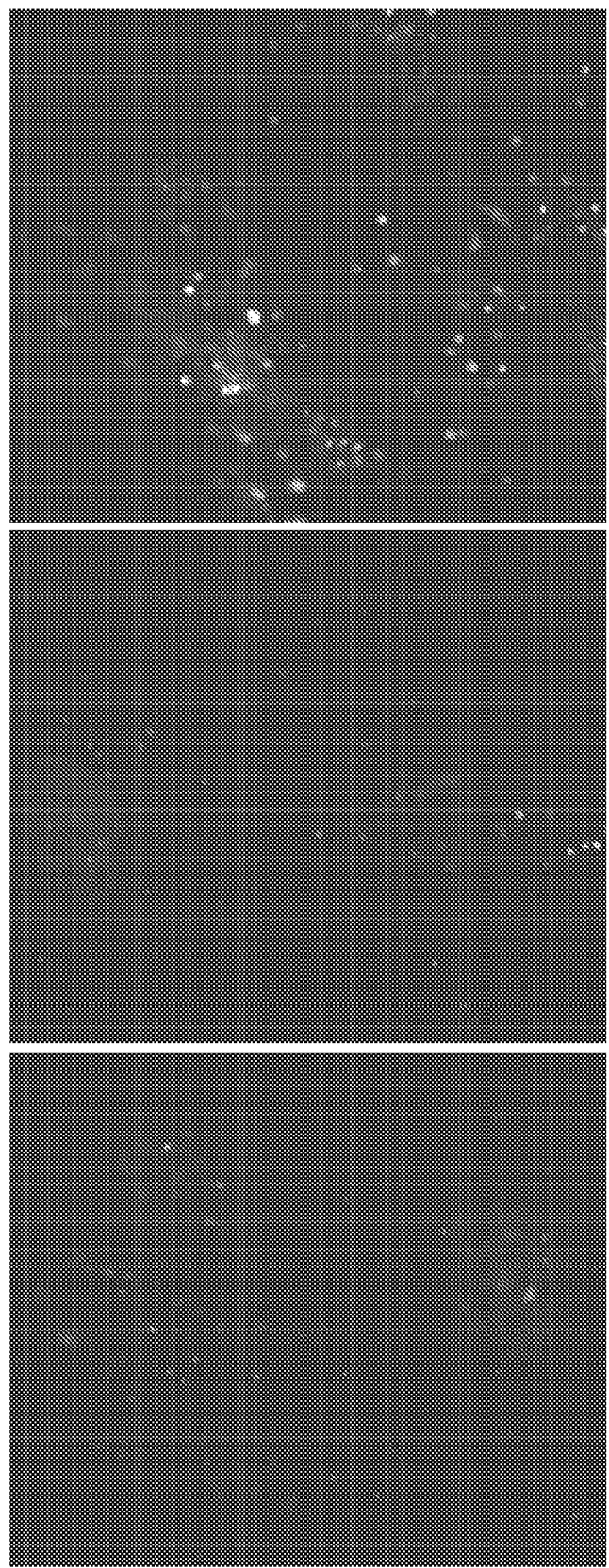
FIG. 12 shows that class I HDAC specific inhibitor MS-275 is not effective in inducing autophagy. Hela cells were treated with DMSO, MS-275, or TSA, and then immunostained with anti-LC3 antibodies.

Combination of HDAC10 Inhibitor and an AMPK Inhibitor Results in Inhibition of Cell Growth HDACs inhibitors are potent anti-tumor agents. The anti-proliferative activity of HDACI is generally associated with their nuclear targets important for gene transcription and chromatin remodeling (Drummond et al. (2005) *Annu Rev Pharmacol Toxicol* 45: 495-528). The prominent growth inhibitory phenotype caused by the inactivation of mitochondrial HDAC10 prompted us to determine if HDACI treatment would affect mitochondrial functions and induce metabolic stress response. We found that treatment with a pan HDAC inhibitor, TSA, led to prominent reductions in cellular ATP levels (FIG. 3A) and accumulation of ROS (FIG. 3C(c)). In addition, we looked at autophagy induction by TSA by incubating Hela cells with vehicle (DMSO) or TSA and immunoblotting for type II LC3. As shown in FIGS. 11B and 11C, TSA treatment led to prominent LC3-positive vesicles, indicating autophagy induction. In contrast, MS-275, a class I HDAC-selective inhibitor that does not effectively inhibit HDAC10 (Hess-Stumpp et al. (2007) *Int J Biochem Cell Biol* 39: 1388-1405), failed to induce robust autophagy (FIG. 12). In that experiment, Hela cells were treated with DMSO, 0.5 µM MS-275, or 0.2 µM TSA for 12 hours. Induction of autophagy was assessed by immunostaining with anti-LC3 antibodies.

To determine if TSA-induced autophagy could be inhibited by an AMPK inhibitor, Hela cells were incubated with DMSO or TSA (1 µM) and compound C (10 µM) or the CaMKKβ inhibitor STO-609 (2 µM), which can suppress autophagy induced by nutrient starvation (Hoyer-Hansen et al. (2007) *Mol Cell* 25: 193-205; and data not shown), for 12 hours. The induction of autophagy was assessed by immunoblotting for type II LC3. As shown in FIG. 11C, TSA-induced autophagy was effectively inhibited by the AMPK inhibitor compound C, but not by STO-609 (compare lanes 2-4). Altogether, these data demonstrate that HDACI treatment, similar to specific inactivation of HDAC10, induces mitochondrial defects and AMPK-dependent metabolic stress response.

Our results indicate that AMPK and autophagy are activated as part of the metabolic adaptation to energy and metabolic crisis caused by HDACI treatment. If this hypothesis were true, AMPK and autophagy would support tumor cell survival when challenged by HDACI. Accordingly, disabling AMPK or autophagy should sensitize tumor cells to HDACI-induced cell death. Indeed, as shown in FIG. 4E, treatment with the AMPK inhibitor, compound C, and the autophagy inhibitor, 3MA, both markedly enhanced cell death induced by TSA. Similar pro-cell death effects of compound C and 3MA treatment were also observed in HDAC10 knockdown cells (FIG. 4F). These results support the idea that the AMPK-autophagy pathway is activated as part of metabolic stress response that sustains cancer cell survival upon HDACI treatment. Thus, combining HDACI with agents that inhibit AMPK or autophagy could create a more potent therapy to induce tumor cell death.

Example 11

Figure 8:
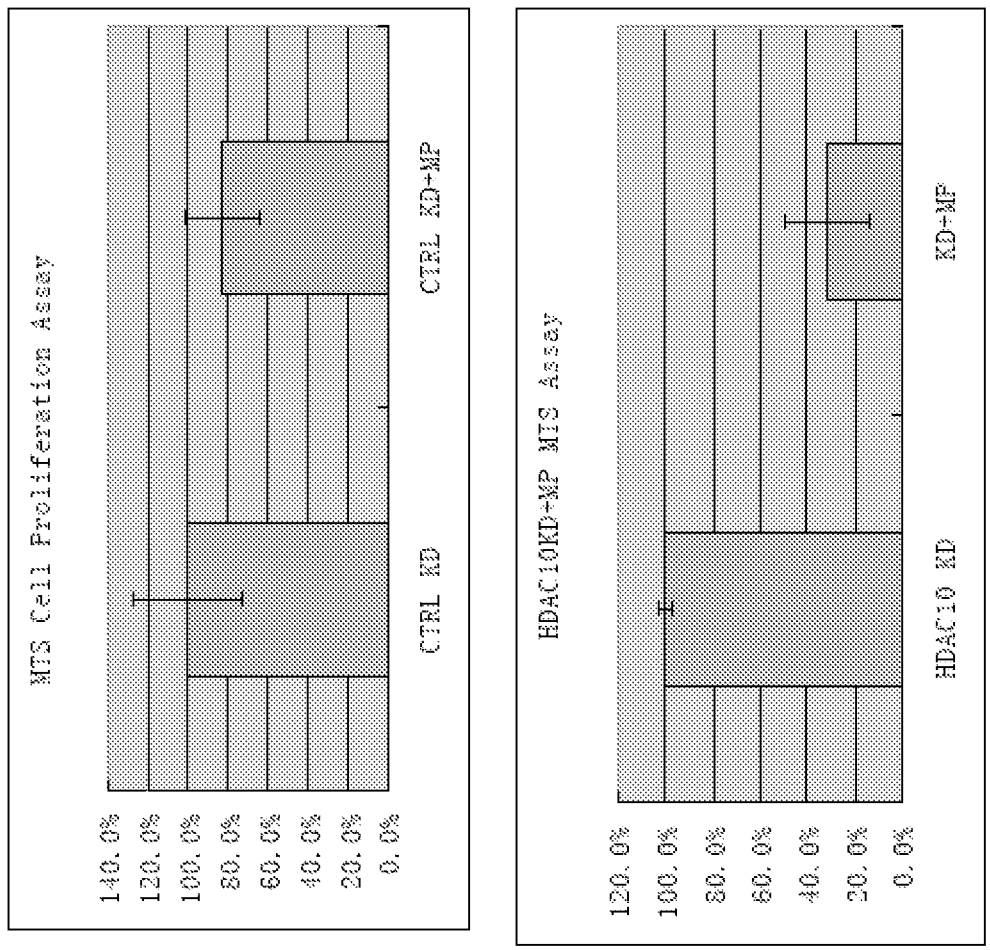
FIG. 8 is a set of graphs demonstrating the increased effectiveness of inhibiting cell growth by treating cells with a combination of an HDAC10 siRNA and methyl pyruvate (MP) together as compared to treating cells with either alone.
Figure 9:
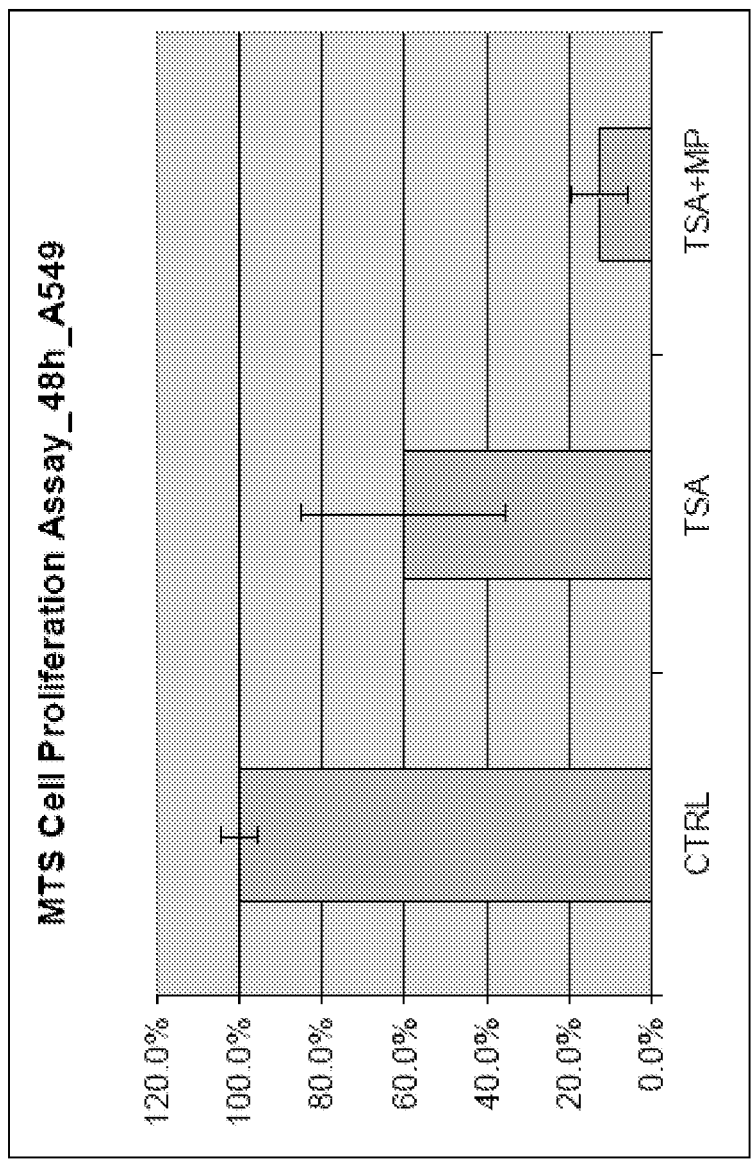
FIG. 9 is a graph showing the increased inhibition of cell growth after treatment with a combination of TSA and MP as compared to treatment with TSA alone.

Combination of HDAC10 Inhibitor and Methyl Pyruvate Results in Inhibition of Cell Growth To further test this model, we treated cells with a combination of an HDACI (TSA or HDAC10 siRNA) and methyl pyruvate. The results are shown in FIGS. 8 and 9. Briefly for the results shown in FIG. 8, A549 cells were transfected with control siRNA or HDAC10 siRNA. Twelve hours after transfection, approximately 5000 cells were placed into wells of a 96 well plate and 3 days later the cells were either mock treated or treated with 10 mM methyl pyruvate (MP) for 24 hours. Living cell numbers were analyzed using the MTS Cell Proliferation Assay. MP alone has no measurable toxicity.

The results shown in FIG. 8 demonstrate a synergistic effect on inhibition of cell growth by the combination of HDAC10 siRNA and MP. A similar assay was performed using TSA as the HDACI in combination with MP. The A549 cells were mocked treated, treated with 0.1 µM TSA or treated with a combination of 0.1 µM TSA and 10 mM MP for 48 hours. The numbers of live cells were analyzed using the MTS Cell Proliferation Assay. MP alone has no effect on cell growth. TSA alone results in reduced cell growth. Treatment with the combination of TSA and MP resulted in significantly improved inhibition of cell growth as compared to TSA or MP treatment alone. See FIG. 9.

Example 12

Figure 14:
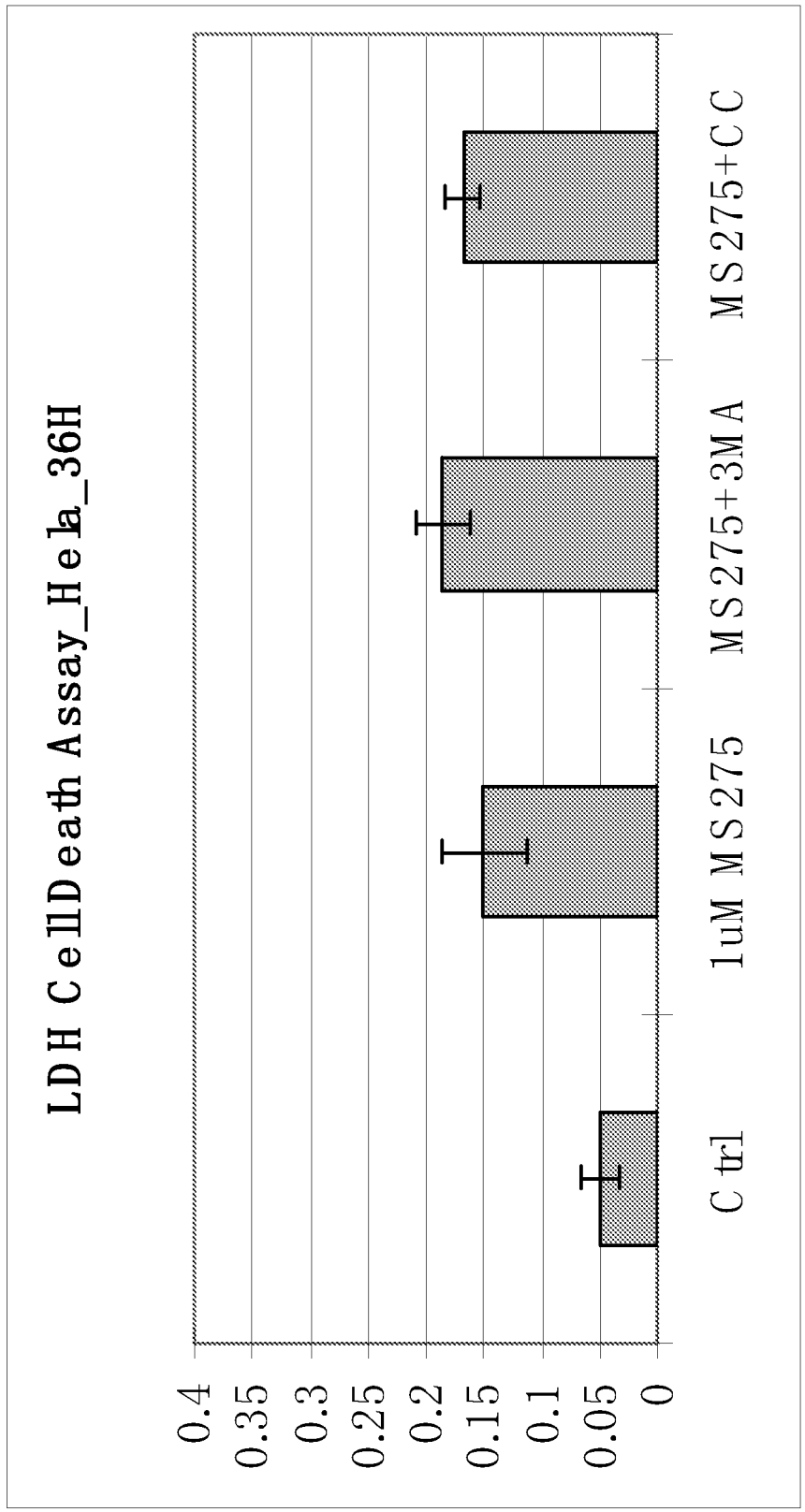
FIG. 14 shows cell death in Hela cells treated with MS275 alone or in combination with 3MA or Compound C(CC), as measured by LDH cytotoxicity assay.

Type I HDAC Inhibitors do Not Synergize with Autophagy Inhibitors or AMPK Inhibitors to Induce Cell Death To confirm that the synergy observed with treatment of cells with a combination of TSA and the AMPK inhibitor, compound C, or the autophagy inhibitor, 3MA, was due to inhibition of a type II HDAC, such as HDAC10, we treated Hela cells with 1 µM MS275, a type I HDAC inhibitor, alone or in combination with 1 µM 3MA or 10 µM compound C. The cells were incubated with MS275 alone for 12 hours, and then with the additional agent, if applicable, for another 24 hours. Cell death was measured using an LDH cytotoxicity assay (Promega CytoTox-96) 36 hours after MS275 treatment was begun. As shown in FIG. 14, the combination of MS275 and 3MA or the combination of MS275 with compound C failed to increase the level of cell death relative to MS275 alone. This result further supports the conclusion that the synergy observed with TSA is due to inhibition of the type II HDAC, HDAC10.

TABLE OF SEQUENCES

| SEQ ID NO | DESCRIPTION | SEQUENCE |
|---|---|---|
| 1 | HDAC10 siRNA #1 | UCCAGUGUGU AAGGCAGCUG CAUCU |
| 2 | HDAC10 siRNA #2 | UGCGCCGUUA GUAAACAUCG CUCAA |
| 3 | HDAC10 siRNA #3 | CGGGUUCUGU GUGUUCAAC |
| 4 | GFP siRNA | CCGACCACAU GAAGCAGCA CGACUU |
| 5 | human HDAC10 amino acid sequence | MGTALVYHED MTATRLLWDD PECEIERPER LTAALDRLRQ RGLEQRCLRL SAREASEEEL GLVHSPEYVS LVRETQVLGK EELQALSGQF DAIYFHPSTF HCARLAAGAG LQLVDAVLTG AVQNGLALVR PPGHHGQRAA ANGFCVFNNV AIAAAHAKQK HGLHRILVVD WDVHHGQGIQ YLFEDDPSVL YFSWHRYEHG RFWPFLRESD ADAVGRGQGL GFTVNLPWNQ VGMGNADYVA AFLHLLLPLA FEFDPELVLV SAGFDSAIGD PEGQMQATPE CFAHLTQLLQ VLAGGRVCAV LEGGYHLESL AESVCMTVQT LLGDPAPPLS GPMAPCQSAL ESIQSARAAQ APHWKSLQQQ DVTAVPMSPS SHSPEGRPPP LLPGGPVCKA AASAPSSLLD QPCLCPAPSV RTAVALTTPD ITLVLPPDVI QQEASALREE TEAWARPHES LAREEALTAL GKLLYLLDGM LDGQVNSGIA ATPASAAAAT LDVAVRRGLS HGAQRLLCVA LGQLDRPPDL AHDGRSLWLN IRGKEAAALS MFHVSTPLPV MTGGFLSCIL GLVLPLAYGF QPDLVLVALG PGHGLQGPHA ALLAAMLRGL AGGRVLALLE ENSTPQLAGI LARVLNGEAP PSLGPSSVAS PEDVQALMYL RGQLEPQWKM LQCHPHLVA |
| 6 | human HDAC10 polynucleotide sequence | ATGGGGACCG CGCTTGTGTA CCATGAGGAC ATGACGGCCA CCCGGCTGCT CTGGGACGAC CCCGAGTGCG AGATCGAGCG TCCTGAGCGC CTGACCGCAG CCCTGGATCG CCTGCGGCAG CGCGGCCTGG AACAGAGGTG TCTGCGGTTG TCAGCCCGCG |

TABLE OF SEQUENCES

| SEQ ID NO | DESCRIPTION | SEQUENCE |
|---|---|---|
| | | AGGCCTCGGA AGAGGAGCTG GGCCTGGTGC ACAGCCCAGA |
| | | GTATGTATCC CTGGTCAGGG AGACCCAGGT CCTAGGCAAG |
| | | GAGGAGCTGC AGGCGCTGTC CGGACAGTTC GACGCCATCT |
| | | ACTTCCACCC GAGTACCTTT CACTGCGCGC GGCTGGCCGC |
| | | AGGGGCTGGA CTGCAGCTGG TGGACGCTGT GCTCACTGGA |
| | | GCTGTGCAAA ATGGGCTTGC CCTGGTGAGG CCTCCCGGGC |
| | | ACCATGGCCA GAGGGCGGCT GCCAACGGGT TCTGTGTGTT |
| | | CAACAACGTG GCCATAGCAG CTGCACATGC CAAGCAGAAA |
| | | CACGGGCTAC ACAGGATCCT CGTCGTGGAC TGGGATGTGC |
| | | ACCATGGCCA GGGGATCCAG TATCTCTTTG AGGATGACCC |
| | | CAGCGTCCTT TACTTCTCCT GGCACCGCTA TGAGCATGGG |
| | | CGCTTCTGGC CTTTCCTGCG AGAGTCAGAT GCAGACGCAG |
| | | TGGGGCGGGG ACAGGGCCTC GGCTTCACTG TCAACCTGCC |
| | | CTGGAACCAG GTTGGGATGG GAAACGCTGA CTACGTGGCT |
| | | GCCTTCCTGC ACCTGCTGCT CCCACTGGCC TTTGAGTTTG |
| | | ACCCTGAGCT GGTGCTGGTC TCGGCAGGAT TTGACTCAGC |
| | | CATCGGGGAC CCTGAGGGGC AAATGCAGGC CACGCCAGAG |
| | | TGCTTCGCCC ACCTCACACA GCTGCTGCAG GTGCTGGCCG |
| | | GCGGCCGGGT CTGTGCCGTG CTGGAGGGCG GCTACCACCT |
| | | GGAGTCACTG GCGGAGTCAG TGTGCATGAC AGTACAGACG |
| | | CTGCTGGGTG ACCCGGCCCC ACCCCTGTCA GGGCCAATGG |
| | | CGCCATGTCA GAGTGCCCTA GAGTCCATCC AGAGTGCCCG |
| | | TGCTGCCCAG GCCCCGCACT GGAAGAGCCT CCAGCAGCAA |
| | | GATGTGACCG CTGTGCCGAT GAGCCCCAGC AGCCACTCCC |
| | | CAGAGGGGAG GCCTCCACCT CTGCTGCCTG GGGGTCCAGT |
| | | GTGTAAGGCA GCTGCATCTG CACCGAGCTC CCTCCTGGAC |
| | | CAGCCGTGCC TCTGCCCCGC ACCCTCTGTC CGCACCGCTG |
| | | TTGCCCTGAC AACGCCGGAT ATCACATTGG TTCTGCCCCC |
| | | TGACGTCATC CAACAGGAAG CGTCAGCCCT GAGGGAGGAG |
| | | ACAGAAGCCT GGGCCAGGCC ACACGAGTCC CTGGCCCGGG |
| | | AGGAGGCCCT CACTGCACTT GGGAAGCTCC TGTACCTCTT |
| | | AGATGGGATG CTGGATGGGC AGGTGAACAG TGGTATAGCA |
| | | GCCACTCCAG CCTCTGCTGC AGCAGCCACC CTGGATGTGG |
| | | CTGTTCGGAG AGGCCTGTCC CACGGAGCCC AGAGGCTGCT |
| | | GTGCGTGGCC CTGGACAGC TGGACCGGCC TCCAGACCTC |
| | | GCCCATGACG GGAGGAGTCT GTGGCTGAAC ATCAGGGGCA |
| | | AGGAGGCGGC TGCCCTATCC ATGTTCCATG TCTCCACGCC |
| | | ACTGCCAGTG ATGACCGGTG GTTTCCTGAG CTGCATCTTG |
| | | GGCTTGGTGC TGCCCCTGGC CTATGGCTTC CAGCCTGACC |
| | | TGGTGCTGGT GGCGCTGGGG CCTGGCCATG GCCTGCAGGG |
| | | CCCCCACGCT GCACTCCTGG CTGCAATGCT TCGGGGGCTG |
| | | GCAGGGGGCC GAGTCCTGGC CCTCCTGGAG GAGAACTCCA |
| | | CACCCCAGCT AGCAGGGATC CTGGCCCGGG TGCTGAATGG |
| | | AGAGGCACCT CCTAGCCTAG GCCCTTCCTC TGTGGCCTCC |
| | | CCAGAGGACG TCCAGGCCCT GATGTACCTG AGAGGGCAGC |
| | | TGGAGCCTCA GTGGAAGATG TTGCAGTGCC ATCCTCACCT |
| | | GGTGGCTTGA |

We claim:

1. A method of inhibiting cancer cell growth comprising contacting the cancer cell with at least one HDAC10 inhibitor and at least one second inhibitor selected from an autophagy inhibitor and an AMPK inhibitor, wherein the cancer is selected from lung, cervical, prostate, and ovarian cancer.

2. The method of claim 1, wherein at least one HDAC10 inhibitor is a pan HDAC inhibitor.

3. The method of claim 2, wherein the pan HDAC10 inhibitor is selected from hydroxamic acid based HDAC inhibitors, suberoylanilide hydroxamic acid (SAHA) and its derivatives, NVP-LAQ824, LBH589, trichostatin A, scriptaid, m-carboxycinnamic acid bishydroxamic acid (CBHA), ABHA, pyroxamide, propenamides, oxamflatin, 6-(3-Chlorophenylureido)caproic hydroxamic acid (3-CI-UCHA), A-161906, jnj16241199, tubacin and tubacin analogs, short chain fatty acid HDAC inhibitors, butyrate, phenylbutyrate, hydroxamic acid, trichostatins, epoxyketone-containing cyclic tetrapeptides, HC-toxin, chlamydocin, diheteropeptide, WF-3161, Cyl-1, Cyl-2, non-epoxyketone-containing cyclic tetrapeptides, apicidin, cyclic-hydroxamic-acid-containing peptides (CHAPS), benzamides and benzamide analogs, CI-994, trapoxin, deprudecin, and organosulfur compounds.

4. The method of claim 1, wherein the autophagy inhibitor is selected from chloroquine or 3-methyladenine.

5. The method of claim 1, wherein the AMPK inhibitor is Compound C.

6. The method of claim 1, wherein the cell is contacted in a subject.

7. The method of claim 6, wherein the subject is human.

8. A method of treating cancer comprising administering to a subject at least one HDAC10 inhibitor and at least one second inhibitor selected from an autophagy inhibitor and an AMPK inhibitor, wherein the cancer is selected from lung, cervical, prostate, and ovarian cancer.

9. The method of claim 8, wherein at least one HDAC10 inhibitor is a pan HDAC inhibitor.

10. The method of claim 9, wherein the pan HDAC10 inhibitor is selected from hydroxamic acid based HDAC inhibitors, suberoylanilide hydroxamic acid (SAHA) and its derivatives, NVP-LAQ824, LBH589, trichostatin A, scriptaid, m-carboxycinnamic acid bishydroxamic acid (CBHA), ABHA, pyroxamide, propenamides, oxamflatin, 6-(3-Chlorophenylureido)caproic hydroxamic acid (3-CI-UCHA), A-161906, jnj16241199, tubacin and tubacin analogs, short chain fatty acid HDAC inhibitors, butyrate, phenylbutyrate, hydroxamic acid, trichostatins, epoxyketone-containing cyclic tetrapeptides, HC-toxin, chlamydocin, diheteropeptide, WF-3161, Cyl-1, Cyl-2, non-epoxyketone-containing cyclic tetrapeptides, apicidin, cyclic-hydroxamic-acid-containing peptides (CHAPS), benzamides and benzamide analogs, CI-994, trapoxin, deprudecin, and organosulfur compounds.

11. The method of claim 8, wherein the autophagy inhibitor is selected from chloroquine or 3-methyladenine.

12. The method of claim 8, wherein the AMPK inhibitor is Compound C.

13. A method of inhibiting cancer cell growth comprising contacting the cancer cell with at least one HDAC10 inhibitor and methylpyruvate, wherein the cancer is lung cancer.

14. The method of claim 13, wherein at least one HDAC10 inhibitor is a pan HDAC inhibitor.

15. The method of claim 14, wherein the pan HDAC10 inhibitor is selected from hydroxamic acid based HDAC inhibitors, suberoylanilide hydroxamic acid (SAHA) and its derivatives, NVP-LAQ824, LBH589, trichostatin A, scriptaid, m-carboxycinnamic acid bishydroxamic acid (CBHA), ABHA, pyroxamide, propenamides, oxamflatin, 6-(3-Chlorophenylureido)caproic hydroxamic acid (3-CI-UCHA), A-161906, jnj16241199, tubacin and tubacin analogs, short chain fatty acid HDAC inhibitors, butyrate, phenylbutyrate, hydroxamic acid, trichostatins, epoxyketone-containing cyclic tetrapeptides, HC-toxin, chlamydocin, diheteropeptide, WF-3161, Cyl-1, Cyl-2, non-epoxyketone-containing cyclic tetrapeptides, apicidin, cyclic-hydroxamic-acid-containing peptides (CHAPS), benzamides and benzamide analogs, CI-994, trapoxin, deprudecin, and organosulfur compounds.

16. The method of claim 13, wherein the cell is contacted in a subject.

17. The method of claim 16, wherein the subject is human.

18. A method of treating cancer comprising administering to a subject at least one HDAC10 inhibitor and methylpyruvate, wherein the cancer is lung cancer.

19. The method of claim 18, wherein at least one HDAC10 inhibitor is a pan HDAC inhibitor.

20. The method of claim 19, wherein the pan HDAC10 inhibitor is selected from hydroxamic acid based HDAC inhibitors, suberoylanilide hydroxamic acid (SAHA) and its derivatives, NVP-LAQ824, LBH589, trichostatin A, scriptaid, m-carboxycinnamic acid bishydroxamic acid (CBHA), ABHA, pyroxamide, propenamides, oxamflatin, 6-(3-Chlorophenylureido)caproic hydroxamic acid (3-CI-UCHA), A-161906, jnj16241199, tubacin and tubacin analogs, short chain fatty acid HDAC inhibitors, butyrate, phenylbutyrate, hydroxamic acid, trichostatins, epoxyketone-containing cyclic tetrapeptides, HC-toxin, chlamydocin, diheteropeptide, WF-3161, Cyl-1, Cyl-2, non-epoxyketone-containing cyclic tetrapeptides, apicidin, cyclic-hydroxamic-acid-containing peptides (CHAPS), benzamides and benzamide analogs, CI-994, trapoxin, deprudecin, and organosulfur compounds.

* * * * *